(12) United States Patent
Li et al.

(10) Patent No.: US 9,333,048 B2
(45) Date of Patent: May 10, 2016

(54) METHODS, SYSTEMS, AND PRODUCTS FOR MONITORING HEALTH

(71) Applicants: Kevin A. Li, New York, NY (US); Troy C. Meuninck, Newnan, GA (US); Robert Raymond Miller, II, Convent Station, NJ (US); James H. Pratt, Round Rock, AZ (US); Horst J. Schroeter, New Providence, NJ (US); Behzad Shahraray, Holmdel, NJ (US)

(72) Inventors: Kevin A. Li, New York, NY (US); Troy C. Meuninck, Newnan, GA (US); Robert Raymond Miller, II, Convent Station, NJ (US); James H. Pratt, Round Rock, AZ (US); Horst J. Schroeter, New Providence, NJ (US); Behzad Shahraray, Holmdel, NJ (US)

(73) Assignee: AT&T INTELLECTUAL PROPERTY I, L.P., Atlanta, GA (US)

(*) Notice: Subject to any disclaimer, the term of this patent is extended or adjusted under 35 U.S.C. 154(b) by 150 days.

(21) Appl. No.: 13/647,426

(22) Filed: Oct. 9, 2012

(65) Prior Publication Data

US 2014/0099594 A1 Apr. 10, 2014

(51) Int. Cl.
| | | |
|---|---|---|
| *A61C 1/00* | (2006.01) | |
| *A61C 17/02* | (2006.01) | |
| *A61C 19/04* | (2006.01) | |
| *A61C 17/22* | (2006.01) | |
| *G06F 19/00* | (2011.01) | |
| *A46B 11/00* | (2006.01) | |

(52) U.S. Cl.
CPC ............ *A61C 1/0015* (2013.01); *A61C 17/0202* (2013.01); *A61C 17/227* (2013.01); *A61C 19/04* (2013.01); *G06F 19/3462* (2013.01); *G06F 19/3475* (2013.01); *A46B 11/001* (2013.01); *A46B 2200/1066* (2013.01)

(58) Field of Classification Search
CPC ..... A61C 1/0015; A61C 17/0202; A61C 19/04
USPC ................ 433/27–31, 80–90, 215–216, 224; 15/167.1
See application file for complete search history.

(56) References Cited

U.S. PATENT DOCUMENTS

| | | | |
|---|---|---|---|
| 5,245,592 A * | 9/1993 | Kuemmel | A61C 7/00 368/10 |
| 6,623,698 B2 | 9/2003 | Kuo | |
| 7,314,453 B2 | 1/2008 | Kuo | |
| 7,386,333 B1 | 6/2008 | Birecki et al. | |
| 7,890,193 B2 * | 2/2011 | Tingey | A61N 1/36014 607/134 |
| 7,916,282 B2 * | 3/2011 | Duineveld et al. | 356/72 |
| 8,202,230 B2 | 6/2012 | Gatzemeyer et al. | |
| 8,229,676 B2 | 7/2012 | Hyde et al. | |
| 8,807,131 B1 * | 8/2014 | Tunnell | A61M 16/0051 128/200.14 |
| 2003/0076983 A1 | 4/2003 | Cox | |
| 2004/0220498 A1 * | 11/2004 | Li | A61B 5/145 600/584 |
| 2006/0141421 A1 * | 6/2006 | Braunecker et al. | 433/215 |
| 2007/0028453 A1 | 2/2007 | Crow | |
| 2007/0098856 A1 | 5/2007 | LePine | |
| 2008/0255472 A1 | 10/2008 | Kuo | |
| 2010/0279250 A1 * | 11/2010 | Pond | A61C 1/0084 433/80 |
| 2011/0050431 A1 | 3/2011 | Hood et al. | |

(Continued)

*Primary Examiner* — Yogesh Patel
(74) *Attorney, Agent, or Firm* — Scott P. Zimmerman, PLLC

(57) ABSTRACT

Methods, systems, and products monitor a person's regimen for medicinal and dietary restrictions. When the person's regimen requires a liquid medication or supplement, an oral instrument is commanded to dispense a dosage of fluid. The oral instrument stores a reservoir of the fluid. If the oral instrument is a spoon, for example, the spoon may automatically dispense cough syrup or other medicine. A toothbrush, likewise, may automatically dispense mouthwash. A sensor may confirm presence of the oral instrument in the person's mouth, thus ensuring the dosage of fluid is ingested.

13 Claims, 30 Drawing Sheets

(56) References Cited

U.S. PATENT DOCUMENTS

| | | |
|---|---|---|
| 2011/0053283 A1 | 3/2011 | Hood et al. |
| 2011/0054938 A1* | 3/2011 | Hood et al. .................. 705/3 |
| 2011/0291827 A1 | 12/2011 | Baldocchi et al. |
| 2012/0115111 A1 | 5/2012 | Lepine |
| 2013/0080295 A1* | 3/2013 | Dykes .................. A61C 17/221 705/27.1 |

* cited by examiner

METHODS, SYSTEMS, AND PRODUCTS FOR MONITORING HEALTH

COPYRIGHT NOTIFICATION

A portion of the disclosure of this patent document and its attachments contain material which is subject to copyright protection. The copyright owner has no objection to the facsimile reproduction by anyone of the patent document or the patent disclosure, as it appears in the Patent and Trademark Office patent files or records, but otherwise reserves all copyrights whatsoever.

BACKGROUND

Good health is important to all people. We all want to adopt regimens that help ensure a long and happy life. Maintaining a regimen, though, is hard for many people.

BRIEF DESCRIPTION OF THE SEVERAL VIEWS OF THE DRAWINGS

The features, aspects, and advantages of the exemplary embodiments are understood when the following Detailed Description is read with reference to the accompanying drawings, wherein.

DETAILED DESCRIPTION

The exemplary embodiments will now be described more fully hereinafter with reference to the accompanying drawings. The exemplary embodiments may, however, be embodied in many different forms and should not be construed as limited to the embodiments set forth herein. These embodiments are provided so that this disclosure will be thorough and complete and will fully convey the exemplary embodiments to those of ordinary skill in the art. Moreover, all statements herein reciting embodiments, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure).

Thus, for example, it will be appreciated by those of ordinary skill in the art that the diagrams, schematics, illustrations, and the like represent conceptual views or processes illustrating the exemplary embodiments. The functions of the various elements shown in the figures may be provided through the use of dedicated hardware as well as hardware capable of executing associated software. Those of ordinary skill in the art further understand that the exemplary hardware, software, processes, methods, and/or operating systems described herein are for illustrative purposes and, thus, are not intended to be limited to any particular named manufacturer.

As used herein, the singular forms "a," "an," and "the" are intended to include the plural forms as well, unless expressly stated otherwise. It will be further understood that the terms "includes," "comprises," "including," and/or "comprising," when used in this specification, specify the presence of stated features, integers, steps, operations, elements, and/or components, but do not preclude the presence or addition of one or more other features, integers, steps, operations, elements, components, and/or groups thereof. It will be understood that when an element is referred to as being "connected" or "coupled" to another element, it can be directly connected or coupled to the other element or intervening elements may be present. Furthermore, "connected" or "coupled" as used herein may include wirelessly connected or coupled. As used herein, the term "and/or" includes any and all combinations of one or more of the associated listed items.

It will also be understood that, although the terms first, second, etc. may be used herein to describe various elements, these elements should not be limited by these terms. These terms are only used to distinguish one element from another. For example, a first device could be termed a second device, and, similarly, a second device could be termed a first device without departing from the teachings of the disclosure.

Figure 1:
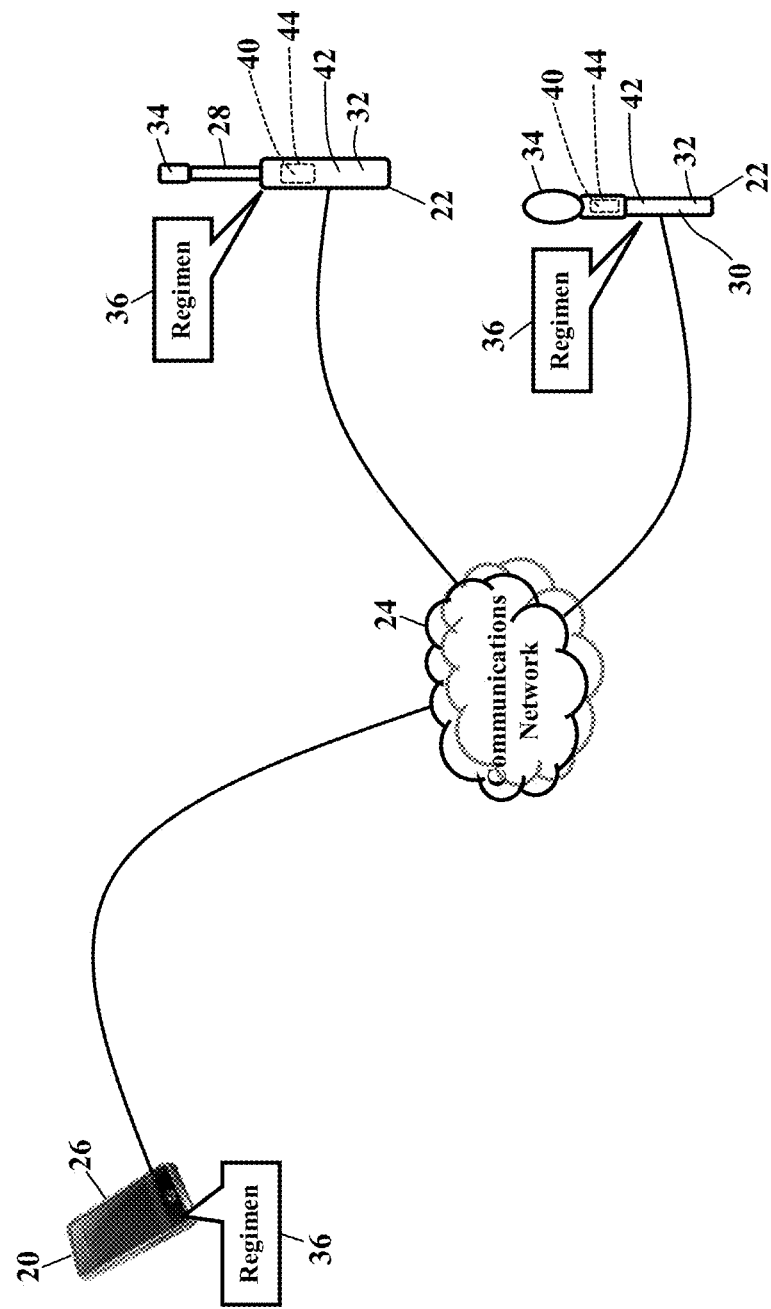
FIG. 1 is a simplified schematic illustrating an environment in which exemplary embodiments may be implemented.

FIG. 1 is a simplified schematic illustrating an environment in which exemplary embodiments may be implemented. A communications device 20 communicates with one or more oral instruments 22 via a communications network 24. The communications device 20 is illustrated as a smart phone 26, but the communications device 20 may be any computer, tablet, server, or any other processor-controlled device. FIG. 1, for simplicity, illustrates one of the oral instruments 22 as an electronic toothbrush 28. Another one of the oral instruments 22 is illustrated as an electronic spoon 30. The oral instrument 22, of course, may be any utensil or device capable of being inserted into an oral cavity of a user. Whatever the oral instrument 22, electronics 32 may analyze fluids and food to help the user maintain a diet. The toothbrush 28, for example, may have one or more sensors 34 that detect the ingredients or characteristics of residual food particles in the mouth or between the bristles. The sensor 34 in the spoon 30 may analyze food scooped into the bowl of the spoon 30. Likewise, if the oral instrument 22 is a fork, the sensor 34 analyze food stabbed by a prong. Regardless, the electronics 32 analyze sensor outputs from the sensor 34 to help the user track an amount of food consumed and/or a type of food consumed. The sensor 34, for example, may sense any chemical compound. Intake of salts (chlorides) and glucose, for example, may help monitor and determine hypertension, high blood pressure, and diabetes. Temperature in the mouth may be sensed to predict ovulation. DNA/RNA may be sensed, collected, and/or analyzed to determine genomic information. The nutritional content of foods may be determined, based on their chemical composition. Whatever the sensor 34 senses, the sensor outputs may be compared to a regimen 36. The regimen 36 describes any dietary plan, restriction, or medicinal schedule. The oral instrument 22 may thus be used to monitor ingestion for adherence to the regimen 36.

The oral instrument 22 may also dispense a fluid 40. The oral instrument 22 may have an injector mechanism 42 that is capable of dispensing the fluid 40 from a fluid reservoir 44. That is, as the oral instrument 22 is used, the fluid 40 may be dispensed into a mouth of the user. So, as the user brushes her teeth, for example, the toothbrush 28 may automatically dispense mouthwash or fluoride. If the user needs cough medicine, the spoon 30 may automatically dispense the cough medicine. Whatever the fluid 40, the oral instrument 22 may dispense the fluid 40 according to the regimen 36, as later paragraphs will explain.

The oral instrument 22 may thus help enforce the regimen 36. Many people have difficulty following the often rigid requirements of a medicinal plan. The oral instrument 22, however, helps the user adhere to the regimen 36. Because the oral instrument 22 may dispense the fluid 40, the oral instrument 22 may automatically dispense liquid medications. The fluid reservoir 44, for example, may contain cough syrup, liquid antibiotic, or mouthwash. When the user brushes their teeth or ingests food, the oral instrument 22 may inject the fluid 40. The oral instrument 22 may also log each dosage of the fluid 40, and report each dosage to caregivers, as later paragraphs will explain. Exemplary embodiments thus help the user monitor and adhere to their medicinal regimen 36.

The oral instrument 22 also helps enforce dietary needs. The regimen 36, for example, may detail specific foods which should be eaten, and/or avoided, to meet a dietary or exercise goal. The sensor 34 may thus determine the nutritional content of ingested food, and monitor compliance with daily nutritional requirements. Because the oral instrument 22 may dispense the fluid 40, the oral instrument 22 may automatically dispense a liquid appetite suppressant to discourage and reduce consumption. The fluid 40, alternatively, may be a flavor enhancer that complements flavors in food. The fluid 40 may even be a concentrated gravy, liquid spice, or refreshment that is dispensed from the oral instrument 22.

The oral instrument 22 may be locally or remotely controlled. The electronics 32 in the oral instrument 22 may have the capability to locally analyze the regimen 36 and to determine when to dispense the fluid 40. However, because the oral instrument 22 interfaces with the communications device 20, the oral instrument 22 may even send the sensor outputs to the communications device 20 for remote analysis. That is, the communications device 20 may upload the sensor outputs from the sensor 34, and the communications device 20 may compare the sensor outputs to the regimen 36. The communications device 20 may thus send commands to the oral instrument 22. The oral instrument 22 may thus be remotely instructed to analyze food or to dispense the fluid 40.

Exemplary embodiments thus help monitor the user's health. The oral instrument 22 may analyze the food consumed by the user, thus helping the user maintain the dietary or medicinal regimen 36. The oral instrument 22 may also dispense medicinal fluids 40, perhaps again according to the regimen 36. So, as the spoon 30 is used for eating, for example, medicine may be automatically dispensed, thus relieving the user of having to remember to take medication. The oral instrument 22 may even chime, beep, or otherwise alert when medication is due, thus again helping the user maintain the regimen 36. Exemplary embodiments thus remove mental barriers that often prevent people from adhering to their health regimen 36.

Figure 2:
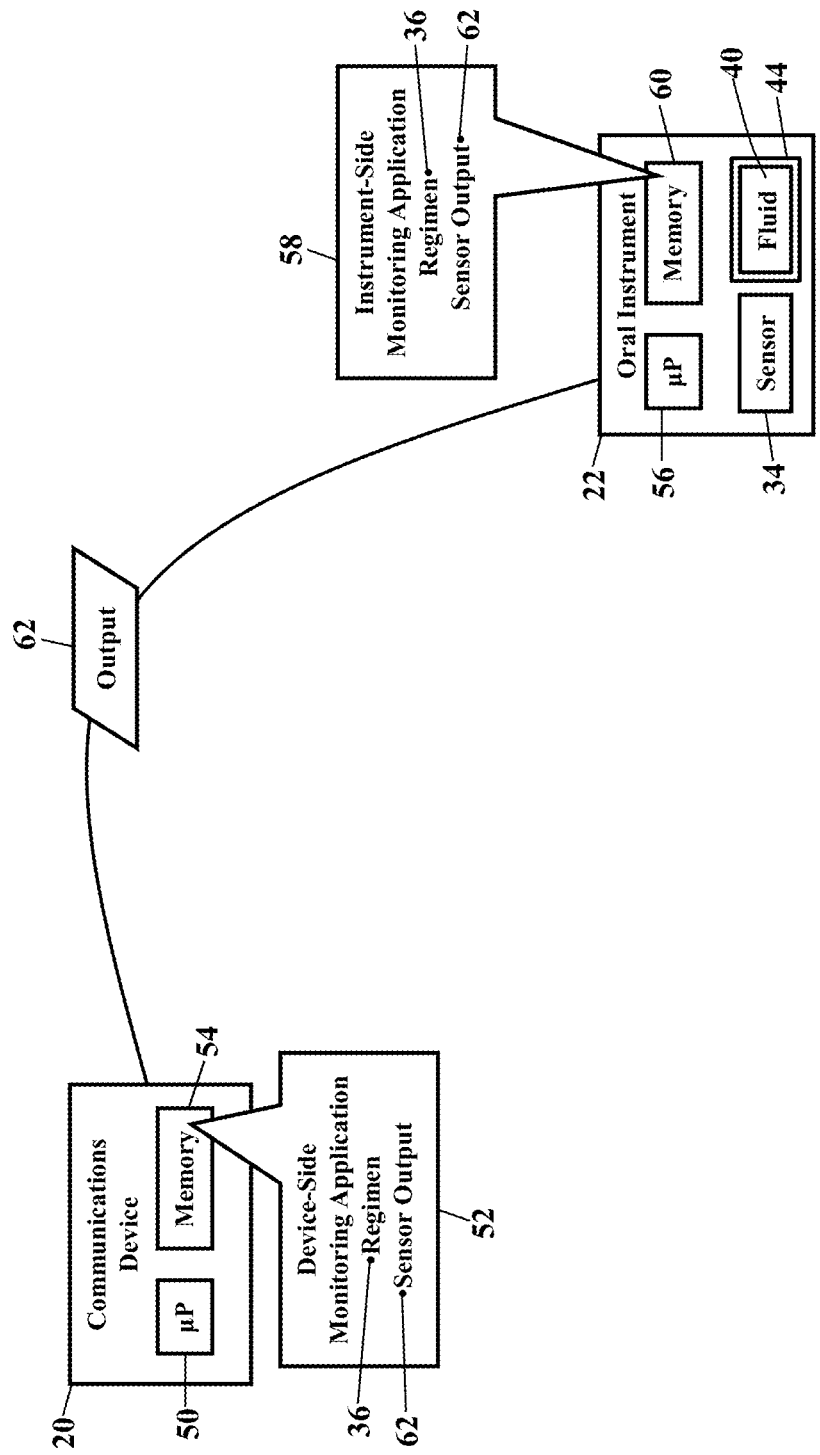
FIG. 2 is a more detailed schematic illustrating an operating environment, according to exemplary embodiments.

FIG. 2 is a more detailed schematic illustrating an operating environment, according to exemplary embodiments. The communications device 20 and the oral instrument 22 may cooperate to help the user adhere to their health regimen 36. The communications device 20 may have a processor 50 (e.g., "μP"), application specific integrated circuit (ASIC), or other component that executes a device-side monitoring application 52 stored in a local memory 54. The oral instrument 22 may also have a processor 56 (e.g., "μP"), application specific integrated circuit (ASIC), or other component that executes an instrument-side monitoring application 58 stored in a memory 60. The device-side monitoring application 52 and the instrument-side monitoring application 58 may thus be instructions, code, and/or programs that cooperate to enforce the regimen 36. The device-side monitoring application 52 and the instrument-side monitoring application 58 may also cooperate to share sensor outputs 62 from the sensor 34 and/or to dispense the fluid 40 from the fluid reservoir 44 in the oral instrument 22.

Exemplary embodiments may be applied regardless of networking environment. The communications network 24 may be a cable network operating in the radio-frequency domain and/or the Internet Protocol (IP) domain. The communications network 24, however, may also include a distributed computing network, such as the Internet (sometimes alternatively known as the "World Wide Web"), an intranet, a local-area network (LAN), and/or a wide-area network (WAN). The communications network 24 may include coaxial cables, copper wires, fiber optic lines, and/or hybrid-coaxial lines. The communications network 24 may even include wireless portions utilizing any portion of the electromagnetic spectrum and any signaling standard (such as the IEEE 802 family of standards, GSM/CDMA/TDMA or any cellular standard, and/or the ISM band). The communications network 24 may even include powerline portions, in which signals are communicated via electrical wiring. The concepts described herein may be applied to any wireless/wireline communications network, regardless of physical componentry, physical configuration, or communications standard(s).

Figure 3:
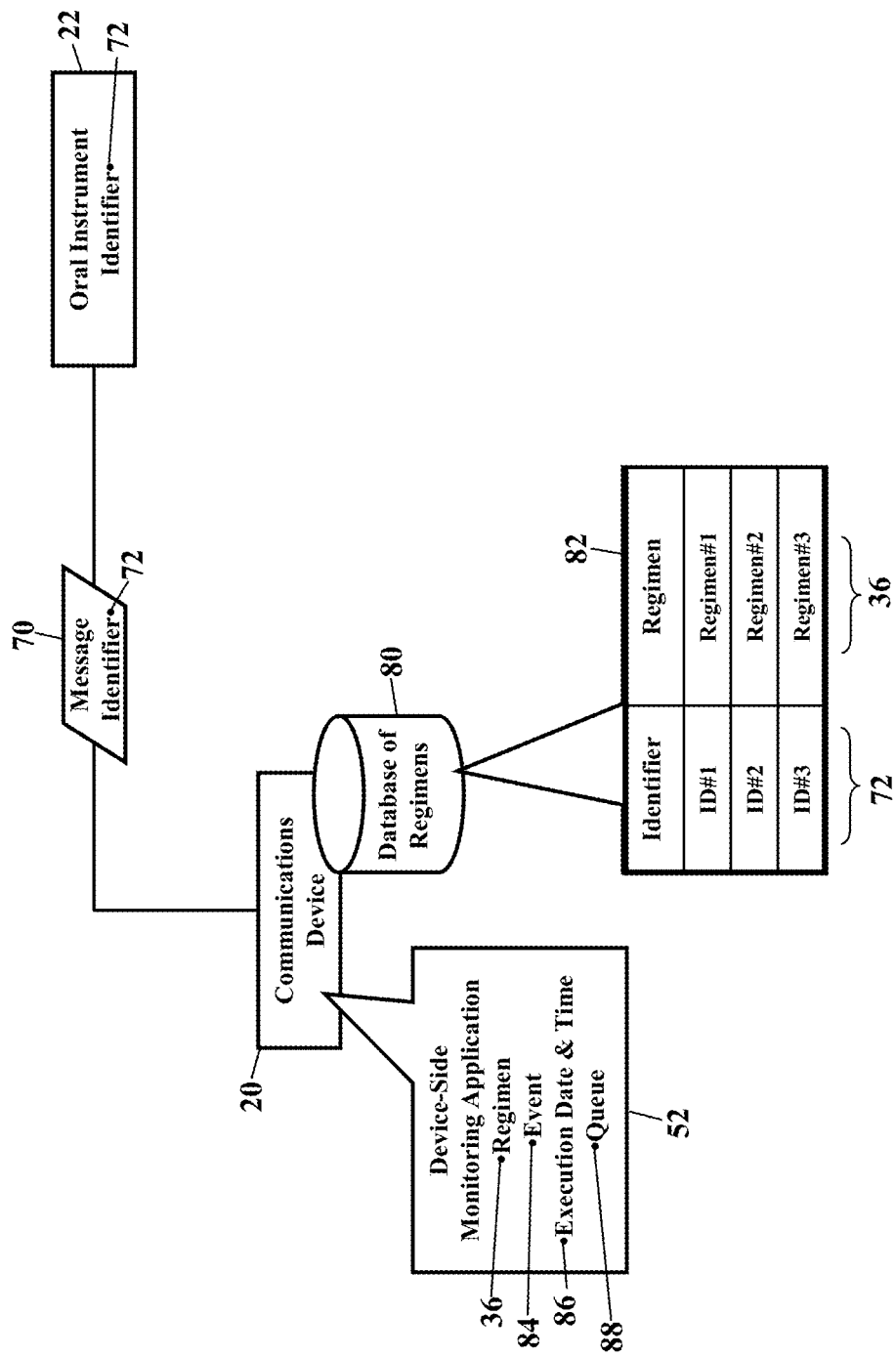
FIG. 3 is a schematic illustrating retrieval of a regimen, according to exemplary embodiments.

FIG. 3 is a schematic illustrating retrieval of the regimen 36, according to exemplary embodiments. Because the communications device 20 and the oral instrument 22 establish wireless and/or wired communication, the oral instrument 22 may send a message 70 to the communications device 20. The message 70 may be an initialization message, a presence message, a registration message, or any other type or function of message. The message 70 routes along the communications network (illustrated as reference numeral 24 in FIG. 1)

to a network address associated with the communications device 20. The message 70 includes an identifier 72 of the oral instrument 22. The identifier 72 is any data or information that uniquely identifies the oral instrument 22 from all other networked devices (such as printers and computers in the user's home). When the communications device 20 receives the message 70, the device-side monitoring application 52 obtains the unique identifier 72 of the oral instrument 22.

The regimen 36 is retrieved. The device-side monitoring application 52 queries a database 80 of regimens for the unique identifier 72 of the oral instrument 22. The database 80 of regimens is illustrated as being locally stored in the communications device 20, but the database 80 of regimens may be remotely stored and accessed. The database 80 of regimens is illustrated as a table 82 that maps, relates, or associates different identifiers 72 to different regimens 36. The device-side monitoring application 52 retrieves the regimen 36 associated with the unique identifier 72 of the oral instrument 22.

The regimen 36 may describe dietary requirements associated with the user. The regimen 36 may describe foods which are prohibited or restricted from consumption. The oral instrument 22, for example, may determine that the user is about to ingest peanuts which cause an allergic reaction. The oral instrument 22 may also determine that the user is about to ingest food having a high glucose measurement. The regimen 36 may thus logically describe dietary restrictions associated with the user of the oral instrument 22. The regimen 36 may be expressed as one or more rules, parameters, and thresholds that logically define dietary requirements.

The regimen 36 may also describe medicinal requirements. The regimen 36 may describe dates and times that medication is required. The regimen 36 may be expressed as one or more events 84 that must be executed at a particular date and time. Oral medication, for example, may be required every four (4) hours. The regimen 36 may thus express the medicinal requirement as the event 84 to be executed once each four hour interval of time. Each event 84 thus has an associated execution date and time 86. The regimen 36 may thus have a queue 88 of events, with each event 84 having its own execution date and time 86. The queue 88 may even be chronologically arranged.

Figure 4:
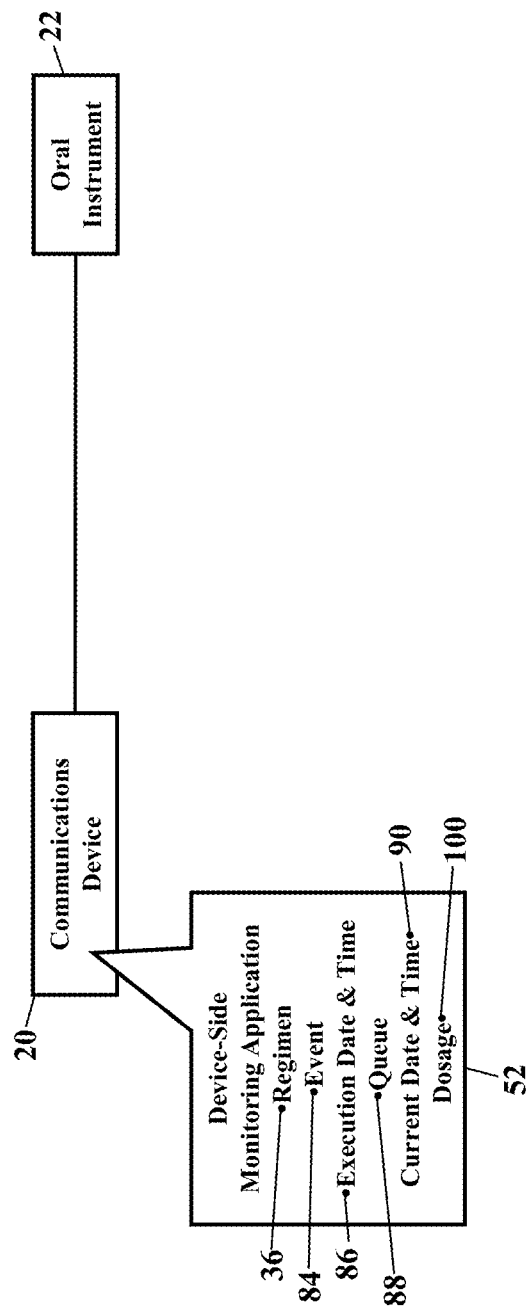
FIG. 4 is a schematic illustrating dosage determinations, according to exemplary embodiments.

FIG. 4 is a schematic illustrating dosage determinations, according to exemplary embodiments. Now that the regimen 36 is known, the device-side monitoring application 52 may inspect the regimen 36 for executable events 84. However the regimen 36 is defined, the regimen 36 may have multiple events 84 that are executed according to the execution date and time 86. The device-side monitoring application 52 accesses a master clock or signal that provides a current date and time 90. The device-side monitoring application 52 may continuously compare the current date and time 90 to the execution dates and times 86 defined in the regimen 36. Each event 84 in the regimen 36 may have the associated execution date and time 86. When the current date and time 90 matches any one of the execution dates and times 86, then the corresponding event 84 is executed by the device-side monitoring application 52.

The event 84, for example, may require a dosage 100. Because the oral instrument 22 may dispense liquid medication (e.g., the fluid 40 illustrated in FIGS. 1-2), the event 84 may require that the oral instrument 22 dispense the dosage 100 from the oral instrument 22. The event 84, for example, may require a teaspoon of cough medicine every four (4) hours. The event 84 may thus describe an amount of the fluid 40 as the dosage 100. The dosage 100 may be expressed in metric or English units. Whatever the event 84, the dosage 100 may be retrieved from the regimen 36.

Figure 5:
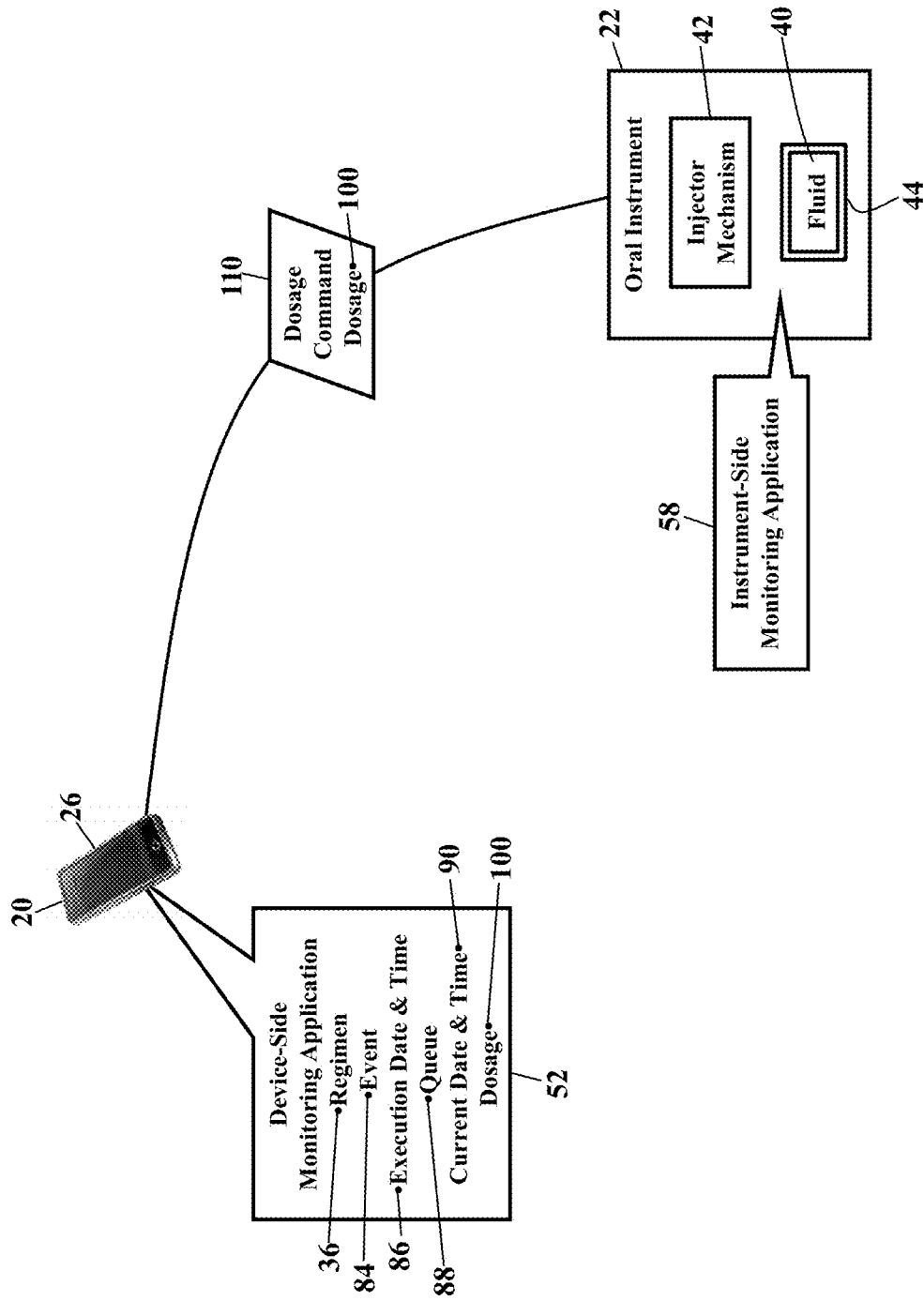
FIG. 5 is a schematic illustrating a dosage command, according to exemplary embodiments.

FIG. 5 is a schematic illustrating a dosage command 110, according to exemplary embodiments. Once the required dosage 100 is determined from the event 84, the device-side monitoring application 52 may instruct the oral instrument 22 to administer the dosage 100. The device-side monitoring application 52 may thus cause the communications device 20 to send a dosage command 110 to the network address associated with the oral instrument 22. The dosage command 110 may describe the dosage 100 required to be dispensed by oral instrument 22. When the oral instrument 22 receives the dosage command 110, the instrument-side monitoring application 58 instructs the injector mechanism 42 to dispense the required dosage 100 from the fluid reservoir 44.

Exemplary embodiments may thus instruct the oral instrument 22 to dispense the fluid 40. As the communications device 20 may continuously inspect the regimen 36, the communications device 20 determines when the dosage 100 is needed. The communications device 20 then instructs the oral instrument 22 to dispense the dosage 100 (e.g., liquid medication, mouthwash, or even sports drink). The oral instrument 22 may thus be remotely commanded to administer the dosage 100. The user's smart phone 26, for example, may download the regimen 36 and monitor the events 84, thus relieving the user of those mental tasks. The regimen 36, however, may also be enforced by a home gateway computer or a cloud-based server. Whatever the communications device 20, at the appropriate time the oral instrument 22 may be commanded to administer the dosage 100 of the fluid 40 from the fluid reservoir 44. Exemplary embodiments may thus remotely monitor and enforce the user's regimen 36 for healthy compliance.

Figure 6:
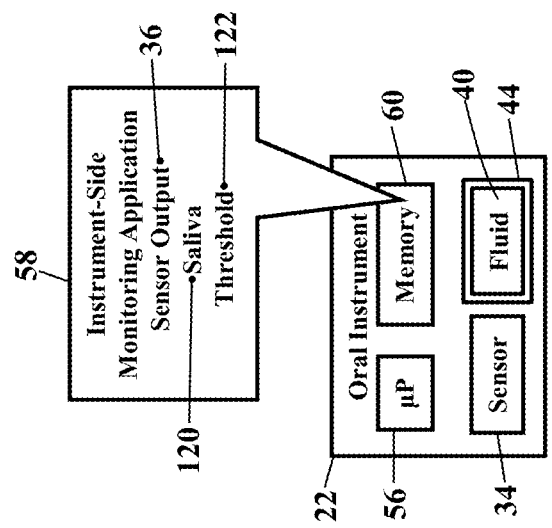
FIGS. 6-7 are schematics illustrating saliva detection, according to exemplary embodiments.
Figure 7:
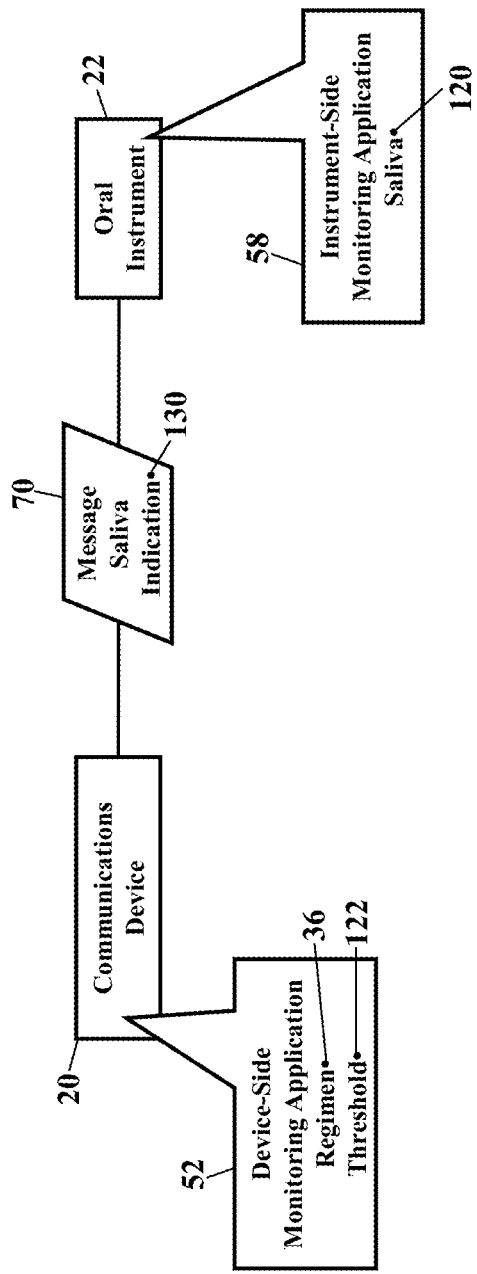

FIGS. 6-7 are schematics illustrating saliva detection, according to exemplary embodiments. Even though the oral instrument 22 may be commanded to dispense the dosage 100, the oral instrument 22 must be in use for effective oral administration. That is, if the oral instrument 22 is not inserted into the user's mouth, the fluid 40 may not be ingested by the user. Indeed, if the oral instrument 22 is merely lying in a drawer, dispensation of the fluid 40 will be useless and messy.

Exemplary embodiments may thus ensure the oral instrument 22 is in use. The oral instrument 22 preferably only dispenses the fluid 40 when inserted into the user's mouth. That is, the oral instrument 22 should only dispense when deliberately used. Exemplary embodiments may thus use the sensor 34 to determine deliberate use. If the oral instrument 22 is determined to be inserted into the user's oral cavity, then dispensation may be authorized.

Exemplary embodiments may detect the presence of saliva 120 in the user's mouth. The sensor 34, for example, may detect the presence of one or more salts, which are commonly found in saliva 120. The sensor 34 obtains its sensor output 62, and the processor 56 may be programmed to interpret the sensor output 62. The instrument-side monitoring application 58, for example, may have one or more chemical thresholds 122 for determining the presence of salts, chlorides, or any other chemical or compound in saliva 120. Whatever chemical is detected, if the threshold 122 is satisfied, then the instrument-side monitoring application 58 may infer that the oral instrument 22 is in deliberate use. That is, the presence of saliva 120 indicates that the oral instrument 22 is placed in the mouth of the user. The instrument-side monitoring application 58 may thus authorize dispensing of the fluid 40. If presence of saliva 120 is not detected, the instrument-side monitoring application 58 may deny dispensing of the fluid 40. So, even of the oral instrument 22 is commanded to dispense the fluid 40 (such as by the dosage command 110 illustrated in FIG. 5), the instrument-side monitoring application 58 may override and deny when saliva 120 is not present.

FIG. 7 illustrates remote notification of the saliva 120. When the instrument-side monitoring application 58 determines the presence of the saliva 120, the instrument-side monitoring application 58 may inform the communications device 20. The message 70 sent from the oral instrument 22, for example, may include a saliva indication 130. When the message 70 is received by the communications device 20, the device-side monitoring application 52 may inspect the message 70 for the saliva indication 130. If the saliva indication 130 indicates that saliva is present, then the device-side monitoring application 52 may commence with retrieving and monitoring the regimen 36 (as earlier paragraphs explained). If, however, the saliva indication 130 indicates that saliva is not present, then the device-side monitoring application 52 may deny dispensing of the fluid 40. Indeed, if saliva is not detected, the device-side monitoring application 52 may decline to retrieve and monitor the regimen 36. There is no need to waste power and processing resources when the oral instrument 22 is not in use.

Figure 8:
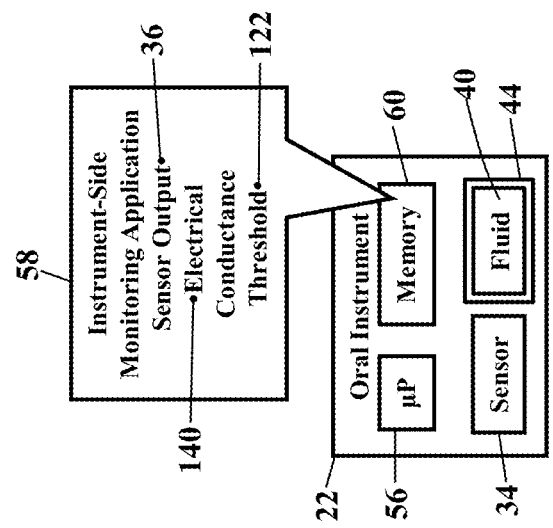
FIGS. 8-9 are schematics illustrating detection of electrical conductance, according to exemplary embodiments.
Figure 9:
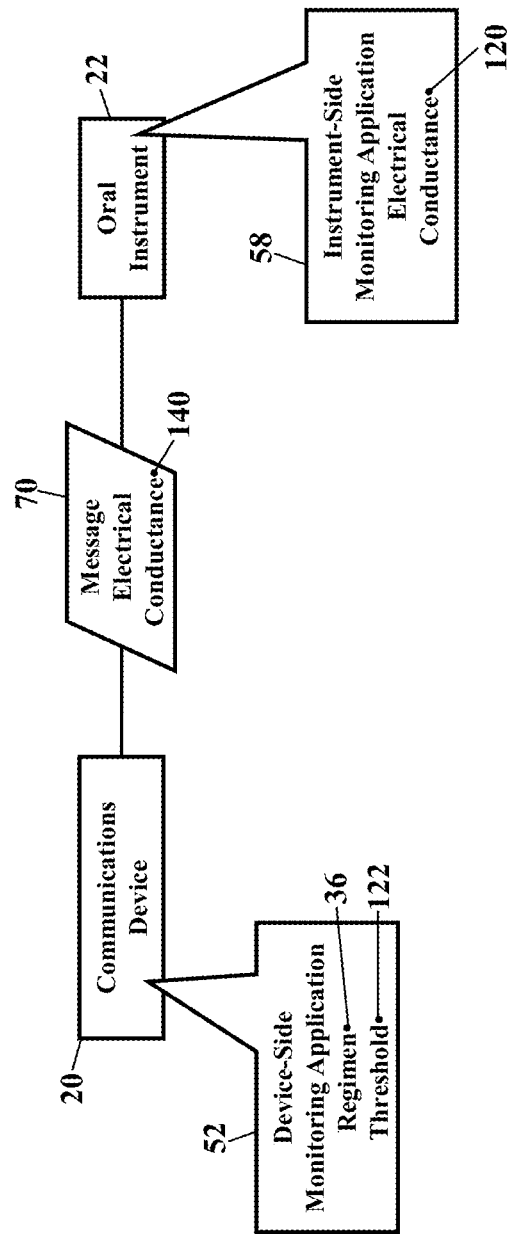

FIGS. 8-9 are schematics illustrating detection of electrical conductance 140, according to exemplary embodiments. Here the instrument-side monitoring application 58 may use the electrical conductance 140 to infer deliberate use of the oral instrument 22. When the oral instrument 22 is placed in the user's mouth, electrical current and/or voltage may be flow and be present between different electrodes. That is, saliva, human tissue, and even toothpaste may conduct electricity. If the sensor 34 detects the electrical conductance 140, then the electrical conductance 140 may be compared to the threshold 122 for conductance values. If the electrical conductance 140 satisfies the threshold 122, the instrument-side monitoring application 58 may infer that the oral instrument 22 is placed in the user's mouth. The instrument-side monitoring application 58 may thus authorize dispensing of the fluid 40. If the electrical conductance 140 is not detected, the instrument-side monitoring application 58 may deny dispensing of the fluid 40. The instrument-side monitoring application 58 may thus ignore or any dosage command 110 when the electrical conductance 140 is not detected.

FIG. 9 illustrates remote notification of the electrical conductance 140. When the instrument-side monitoring application 58 detects the electrical conductance 140, the instrument-side monitoring application 58 may inform the communications device 20. The message 70 sent from the oral instrument 22 may thus include information or data that describes the electrical conductance 140. When the message 70 is received by the communications device 20, the device-side monitoring application 52 may inspect the message 70 for the electrical conductance 140. If the electrical conductance 140 is present, then the device-side monitoring application 52 may commence with retrieving and monitoring the regimen 36 (as earlier paragraphs explained). If, however, the electrical conductance 140 is not present, then the device-side monitoring application 52 may deny dispensing of the fluid 40.

Figure 10:
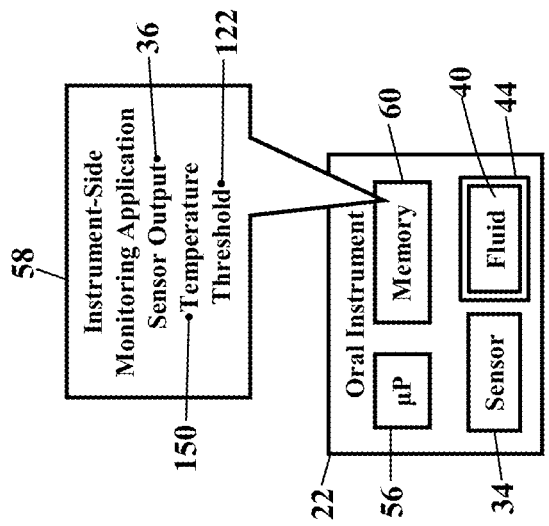
FIGS. 10-11 are schematics illustrating detection of temperature, according to exemplary embodiments.
Figure 11:
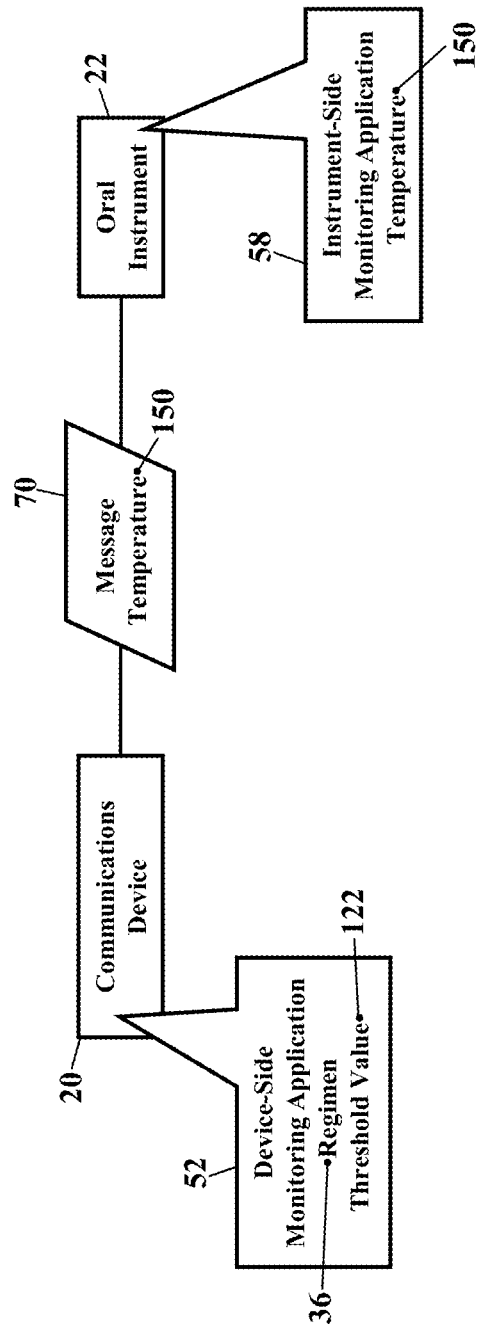

FIGS. 10-11 are schematics illustrating detection of temperature 150, according to exemplary embodiments. Here the sensor 34 may detect the temperature 150 of some portion of the oral instrument 22 to infer deliberate use. The sensor 34, for example, may be positioned within the bristled head of the toothbrush 28, within or near the bowl of the spoon 30, or near a prong of a fork. The temperature 150 detected by the sensor 34 may thus determine whether the oral instrument 22 is placed in the user's mouth. Like a thermometer, temperatures within a range of 98.7 degrees may indicate that the oral instrument 22 is inserted into the user's mouth. A lower temperature (such as room temperature) may indicate the oral instrument 22 is lying in a drawer. The instrument-side monitoring application 58 may compare the temperature 150 to the threshold value 122 (such as about 95 degrees or higher). If the temperature 150 satisfies the threshold value 122, then the instrument-side monitoring application 58 may infer that the oral instrument 22 is placed in the user's mouth. The instrument-side monitoring application 58 may thus authorize dispensing of the fluid 40. If the temperature 150 is less than the threshold value 122, then the instrument-side monitoring application 58 may infer that the oral instrument 22 is not placed in the user's mouth. The instrument-side monitoring application 58 may thus deny dispensing of the fluid 40 and/or ignore or any dosage command 110.

FIG. 11 illustrates remote notification of the temperature 150. When the instrument-side monitoring application 58 receives the temperature 150 from the sensor 34, the instrument-side monitoring application 58 may inform the communications device 20. The message 70 sent from the oral instrument 22 may thus include the temperature 150 detected by the sensor 34. When the message 70 is received by the communications device 20, the device-side monitoring application 52 may itself compare the temperature 150 to the threshold value 122. If the temperature 150 satisfies the threshold value 122, then the device-side monitoring application 52 may infer that the oral instrument 22 is placed in the user's mouth. The device-side monitoring application 52 may thus authorize dispensing of the fluid 40. If the temperature 150 is less than the threshold value 122, then the device-side monitoring application 52 may deny dispensing of the fluid 40. Even if the regimen 36 were to require dispensation, the device-side monitoring application 52 may decline, as the oral instrument 22 is not placed in the user's mouth.

Figure 12:
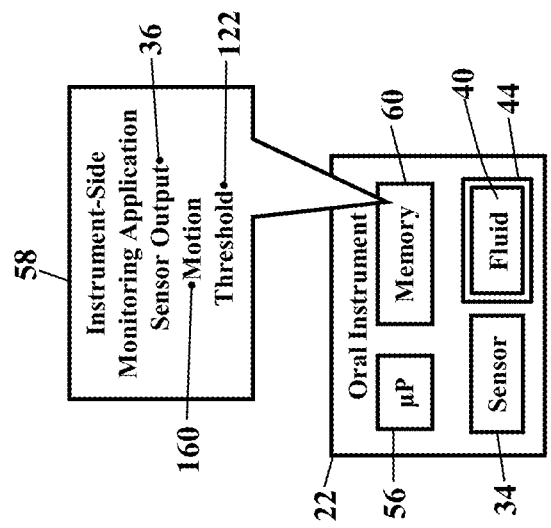
FIGS. 12-13 are schematics illustrating detection of motion, according to exemplary embodiments.
Figure 13:
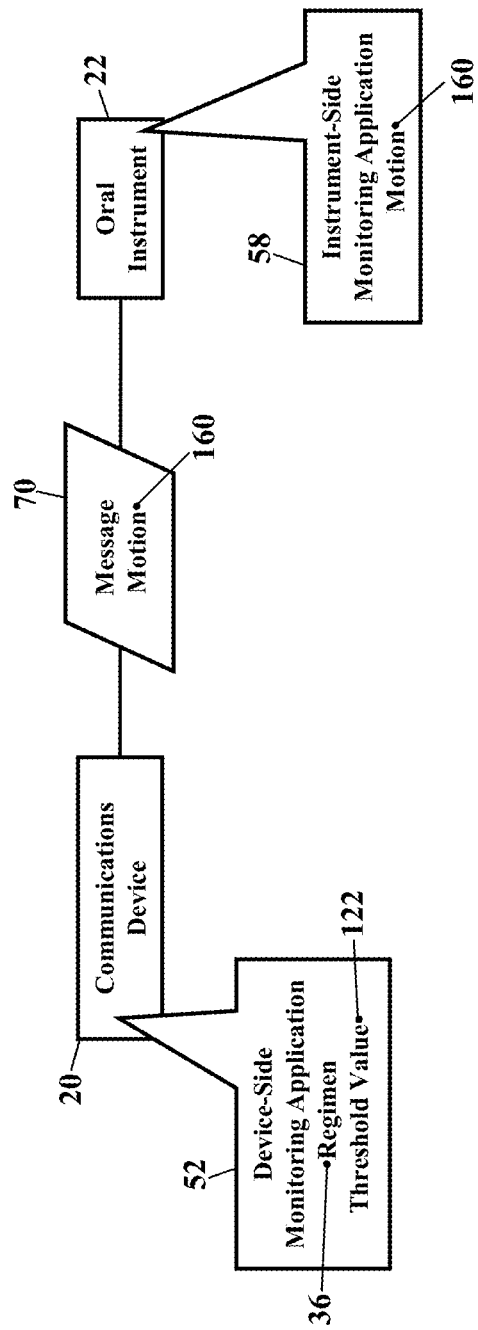

FIGS. 12-13 are schematics illustrating detection of motion 160, according to exemplary embodiments. The sensor 34 may detect the motion 160 of the oral instrument 22. The sensor 34, for example, may be an accelerometer that detects yaw, pitch, and/or roll motions of the oral instrument 22. The motion 160 of the oral instrument 22 may be used to infer deliberate use. A rapid back-and-forth motion, for example, may indicate the toothbrush 28 is brushing teeth in the user's mouth. An arcing movement may indicate the spoon 30 is delivering food into the user's mouth. The instrument-side monitoring application 58 may thus compare the motion 160 to the threshold value 122. Here, though, the threshold value 122 describes one or more yaw, pitch, and/or roll parameters that indicate acceptable movement of the oral instrument 22. If the motion 160 satisfies the threshold value 122, then the instrument-side monitoring application 58 may infer that the oral instrument 22 is placed in the user's mouth. The instrument-side monitoring application 58 may thus authorize dispensing of the fluid 40. If the motion 160 fails the threshold value 122, then the instrument-side monitoring application 58 may infer that the oral instrument 22 is not placed in the user's mouth. The instrument-side monitoring application 58 may thus deny dispensing of the fluid 40 and/or ignore or any dosage command 110.

FIG. 13 illustrates remote notification of the motion 160. Here the motion 160 may be sent to the communications device 20. The message 70 sent from the oral instrument 22 may thus include the motion 160 detected by the sensor 34. When the message 70 is received by the communications device 20, the device-side monitoring application 52 may itself compare the motion 160 to the threshold value 122. If the motion 160 satisfies the threshold value 122, then the device-side monitoring application 52 may infer that the oral instrument 22 is placed in the user's mouth. The device-side monitoring application 52 may thus authorize dispensing of the fluid 40. If the motion 160 fails the threshold value 122, then the device-side monitoring application 52 may deny dispensing of the fluid 40. Even if the regimen 36 were to require dispensation, the device-side monitoring application 52 may decline, as the oral instrument 22 is not placed in the user's mouth.

Figure 14:
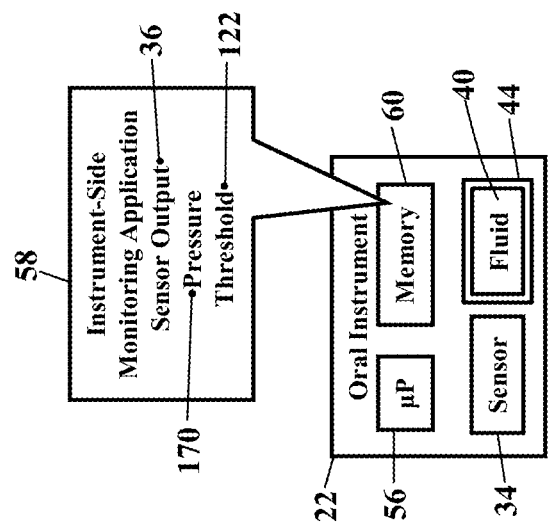
FIGS. 14-15 are schematics illustrating detection of pressure, according to exemplary embodiments.
Figure 15:
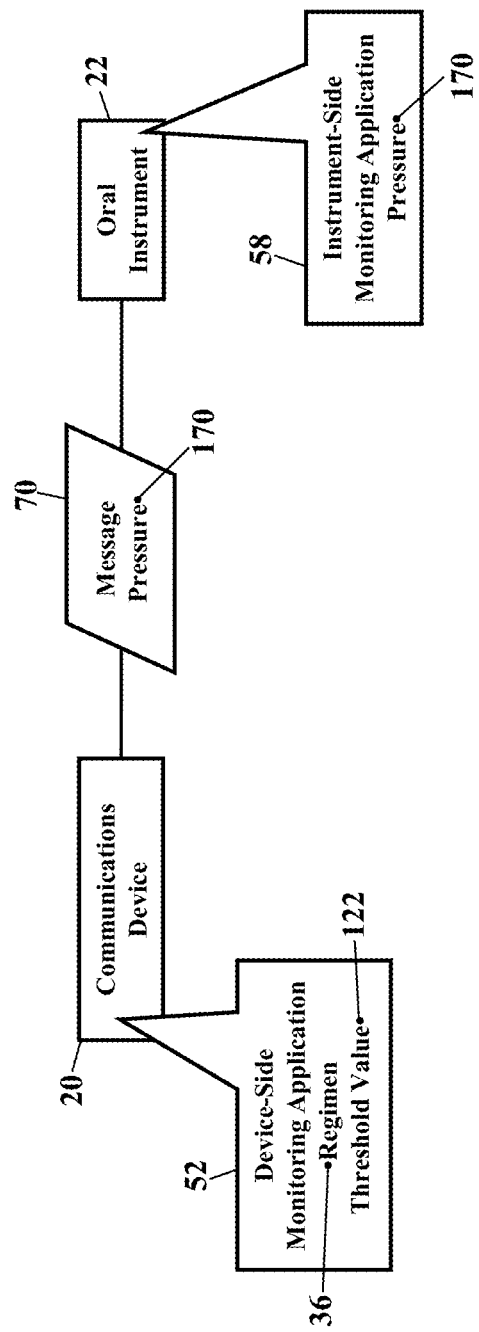

FIGS. 14-15 are schematics illustrating detection of pressure 170, according to exemplary embodiments. Here exemplary embodiments may detect the pressure 170 to infer use of the oral instrument 22. The sensor 34, for example, may detect the pressure 170 applied to a handle of the oral instrument 22. When the user's hand grips the handle, the sensor 34 detects the pressure 170 applied to the handle. The pressure 170 may be used to infer deliberate use. The instrument-side monitoring application 58 compares the pressure 170 to the threshold value 122. Here, though, the threshold value 122 describes some minimum pressure value from which deliberate use may be inferred. If the pressure 170 satisfies the threshold value 122, then the instrument-side monitoring application 58 may infer that the oral instrument 22 is placed in the user's mouth. The instrument-side monitoring application 58 may thus authorize dispensing of the fluid 40. If the pressure 170 fails the threshold value 122, then the instrument-side monitoring application 58 may deny dispensing of the fluid 40 and/or ignore or any dosage command 110.

FIG. 15 illustrates remote notification of the pressure 170. Here the message 70 sent from the oral instrument 22 may include the pressure 170 detected by the sensor 34. When the message 70 is received by the communications device 20, the device-side monitoring application 52 may itself compare the pressure 170 to the threshold value 122. If the pressure 170 satisfies the threshold value 122, then the device-side monitoring application 52 may infer that the oral instrument 22 is placed in the user's mouth. The device-side monitoring application 52 may thus retrieve and monitor the regimen 36 to authorize dispensation of the fluid 40. If, however, the pressure 170 fails the threshold value 122, then the device-side monitoring application 52 may deny dispensing of the fluid 40.

Figure 16:
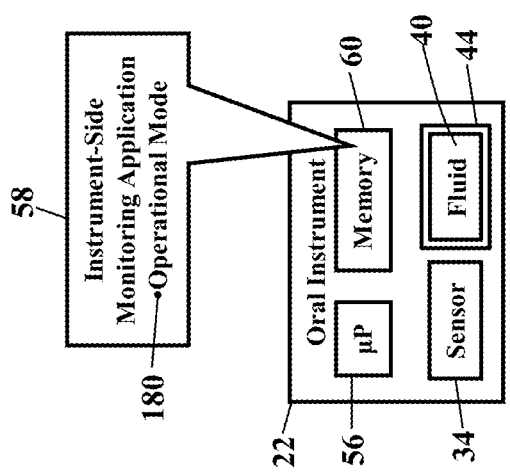
FIGS. 16-17 are schematics illustrating detection of an operational mode, according to exemplary embodiments.
Figure 17:
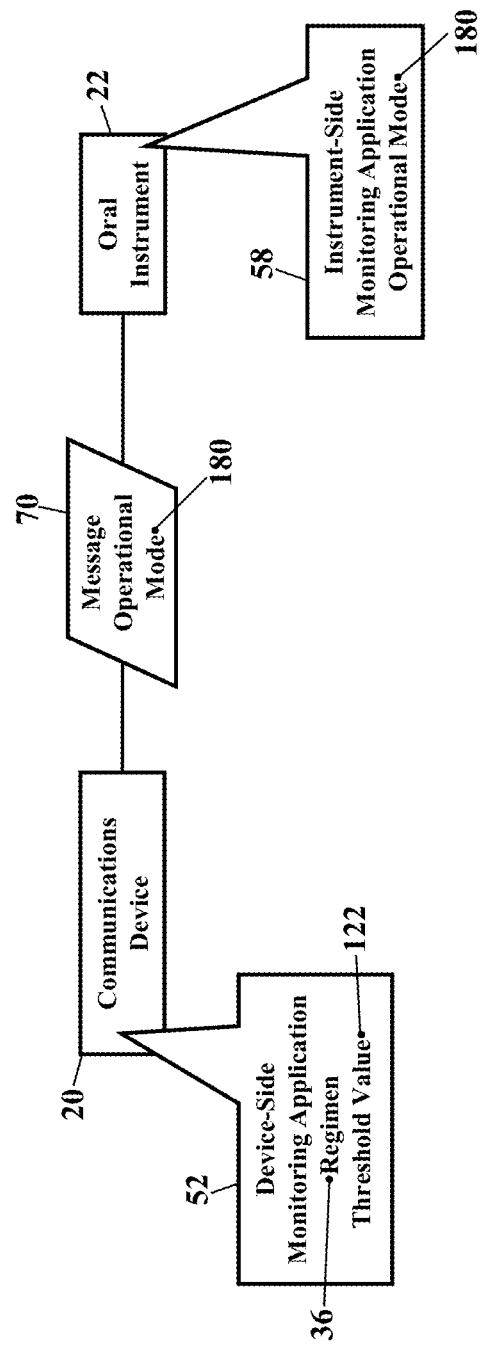

FIGS. 16-17 are schematics illustrating detection of an operational mode 180, according to exemplary embodiments. Here dispensation of the fluid 40 may be authorized simply when the oral instrument 22 is turned "on" by a switch. When the operational mode 180 is true, exemplary embodiments may infer the oral instrument is brushing teeth or lifting food. Exemplary embodiments may thus authorize dispensation. When the operational mode 180 is true, the instrument-side monitoring application 58 may thus authorize dispensing of the fluid 40. If the operational mode 180 is false or "off," then the instrument-side monitoring application 58 may deny dispensing of the fluid 40 and/or ignore or any dosage command 110.

FIG. 17 illustrates remote notification of the operational mode 180. Here the message 70 sent from the oral instrument 22 may include the operational mode 180. When the message 70 is received by the communications device 20, the device-side monitoring application 52 may use the operational mode 180 to authorize or deny dispensation. If the operational mode 180 is true, then the device-side monitoring application 52 may infer that the oral instrument 22 is placed in the user's mouth. The device-side monitoring application 52 may thus retrieve and monitor the regimen 36 to authorize dispensation of the fluid 40. If, however, the operational mode 180 is false, then the device-side monitoring application 52 may deny dispensing of the fluid 40.

Figure 18:
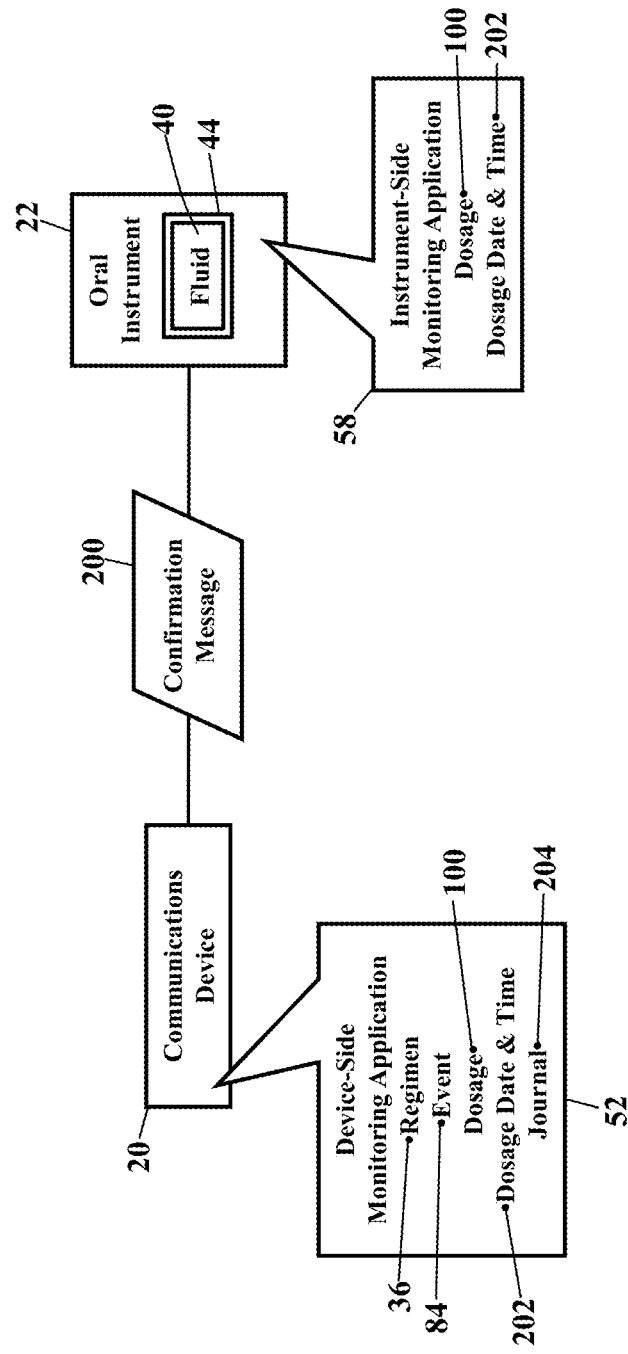
FIG. 18 is a schematic illustrating confirmation of dispensation, according to exemplary embodiments.

FIG. 18 is a schematic illustrating confirmation of dispensation, according to exemplary embodiments. When the oral instrument 22 dispenses the fluid 40, the regimen 36 should be updated. After all, if the regimen 36 is to be a truly useful tool toward recovery and a healthy lifestyle, the regimen 36 should be continuously updated. As any event 84 requires some dispensation of the fluid 40 from the oral instrument 22, exemplary embodiments update the regimen 36 to indicate compliance.

FIG. 18 thus illustrates a confirmation message 200. When the oral instrument 22 dispenses the fluid 40 from the reservoir 44, the instrument-side monitoring application 58 may send the confirmation message 200 to the communications device 20. The confirmation message 200 may include information describing a dosage date and time 202 that the dosage 100 was injected. The confirmation message 200 may also identify the fluid 40, such as by a manufacturer's trade name. The confirmation message 200 routes to the network address associated with the communications device 20. When the confirmation message 200 is received, the device-side monitoring application 52 may log the dosage date and time 202 in an electronic journal 204. The journal 204 thus tracks each dosage 100 of the fluid 40 injected by the oral instrument 22.

Figure 19:
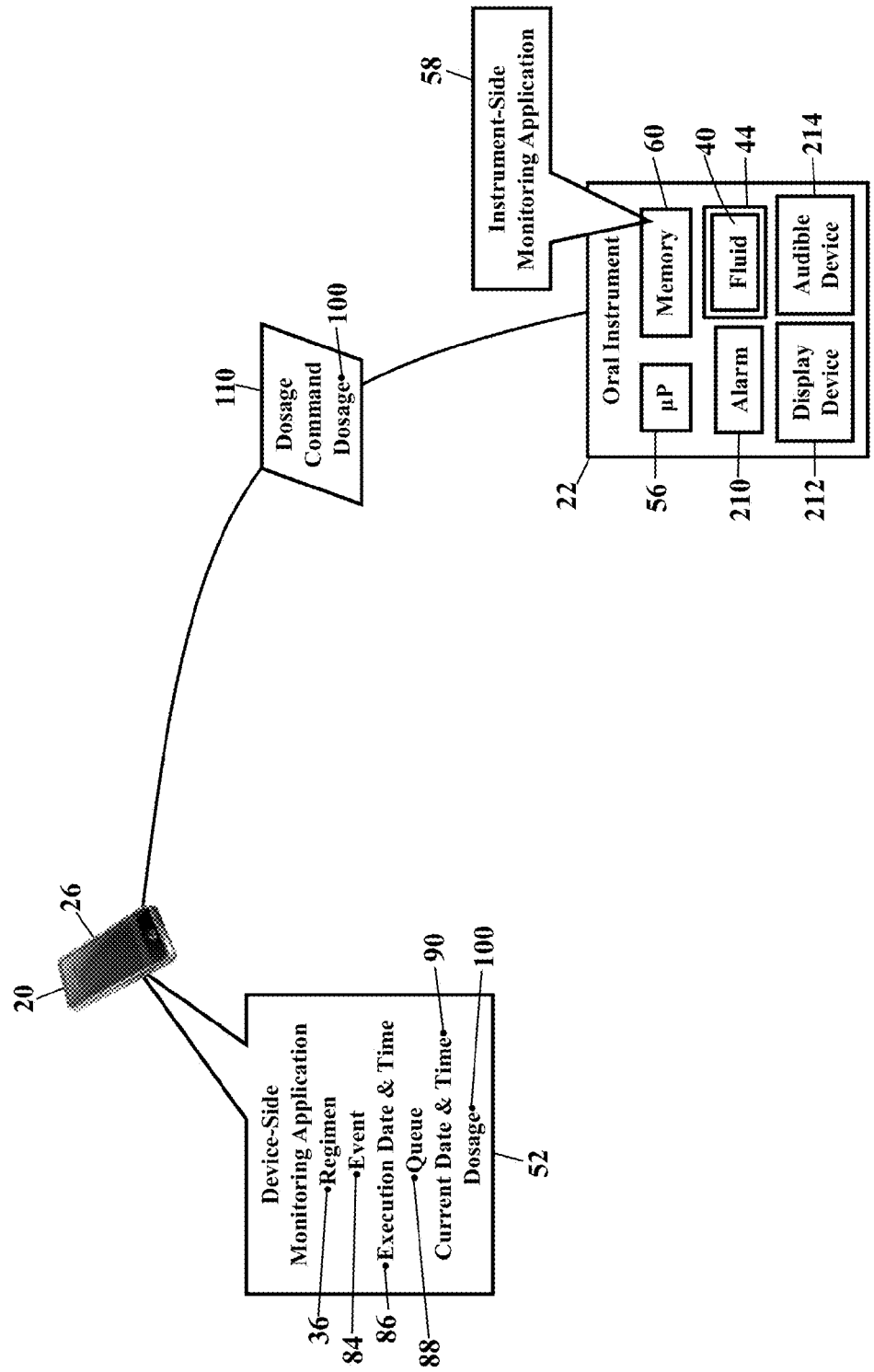
FIG. 19 is a schematic illustrating alarm capabilities, according to exemplary embodiments.

FIG. 19 is a schematic illustrating alarm capabilities, according to exemplary embodiments. Even if the regimen 36 requires the dosage 100, the oral instrument 22 may not be currently in use. The above paragraphs thus explained how the oral instrument 22 may ignore the dosage command 110. Here, though, the oral instrument 22 may chime, buzz, or otherwise alert when it's time to eat, take medication, or brush teeth. When the dosage command 110 is received, exemplary embodiments have determined that the regimen 36 requires the dosage 100 of the fluid 40. The oral instrument 22 may thus activate an alarm 210 to indicate the dosage 100 is due. The instrument-side monitoring application 58 causes the processor 56 to activate the alarm 210 when the dosage command 110 is received, but the oral instrument 22 is determined to be not in use (as earlier paragraphs explained). The alarm 210 may repeat until deliberate use is determined (again as earlier paragraphs explained). The dosage 100 may then be dispensed upon deliberate use. If the oral instrument 22 has a display device 212, the alarm 210 may be visually presented. The alarm 210 may also be audibly presented by an audible device 214, such as a speaker, buzzer, or piezoelectric element.

Figure 20:
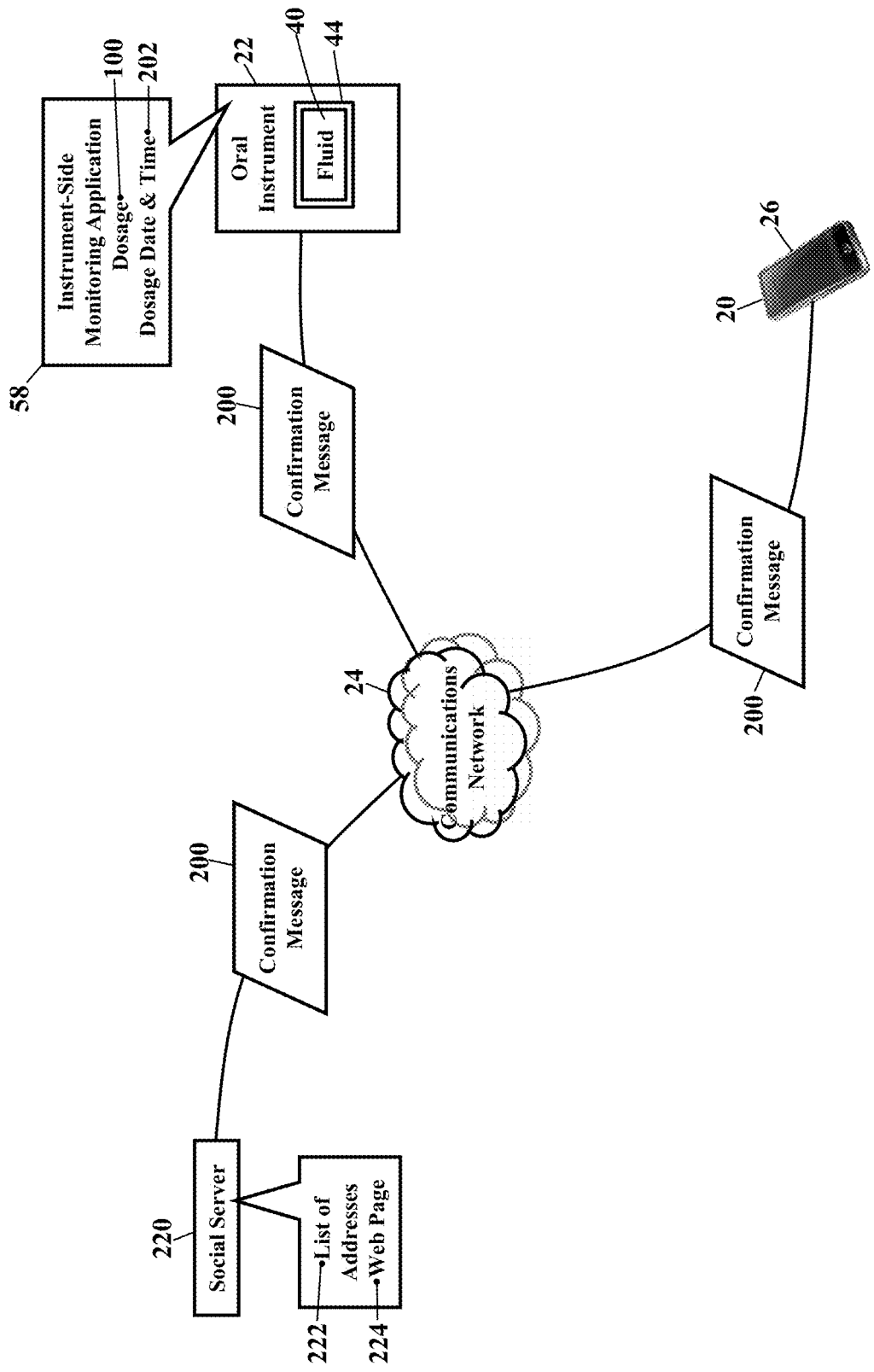
FIG. 20 is a schematic illustrating social postings, according to exemplary embodiments.

FIG. 20 is a schematic illustrating social postings, according to exemplary embodiments. Here the oral instrument 22 and/or the communications device 20 may report the confirmation of the dosage 100 to a social server 220. The social server 220 may then notify a distribution list 222 of addresses that the dosage 100 was successfully administered. The social server 220, for example, may be a web server, email server, text message server, TWITTER® server, or other distribution system. FIG. 20, for simplicity, illustrates the confirmation message 70 routing to the social server 220. The confirmation message 70 may then be posted to the distribution list 222 of addresses. The confirmation message 70 may also be uploaded to a web page 224. Family, friends, and medical personnel may thus be informed of the dispensation. Friends and loved ones may thus confidently know that medicine is being regularly administered.

Figure 21:
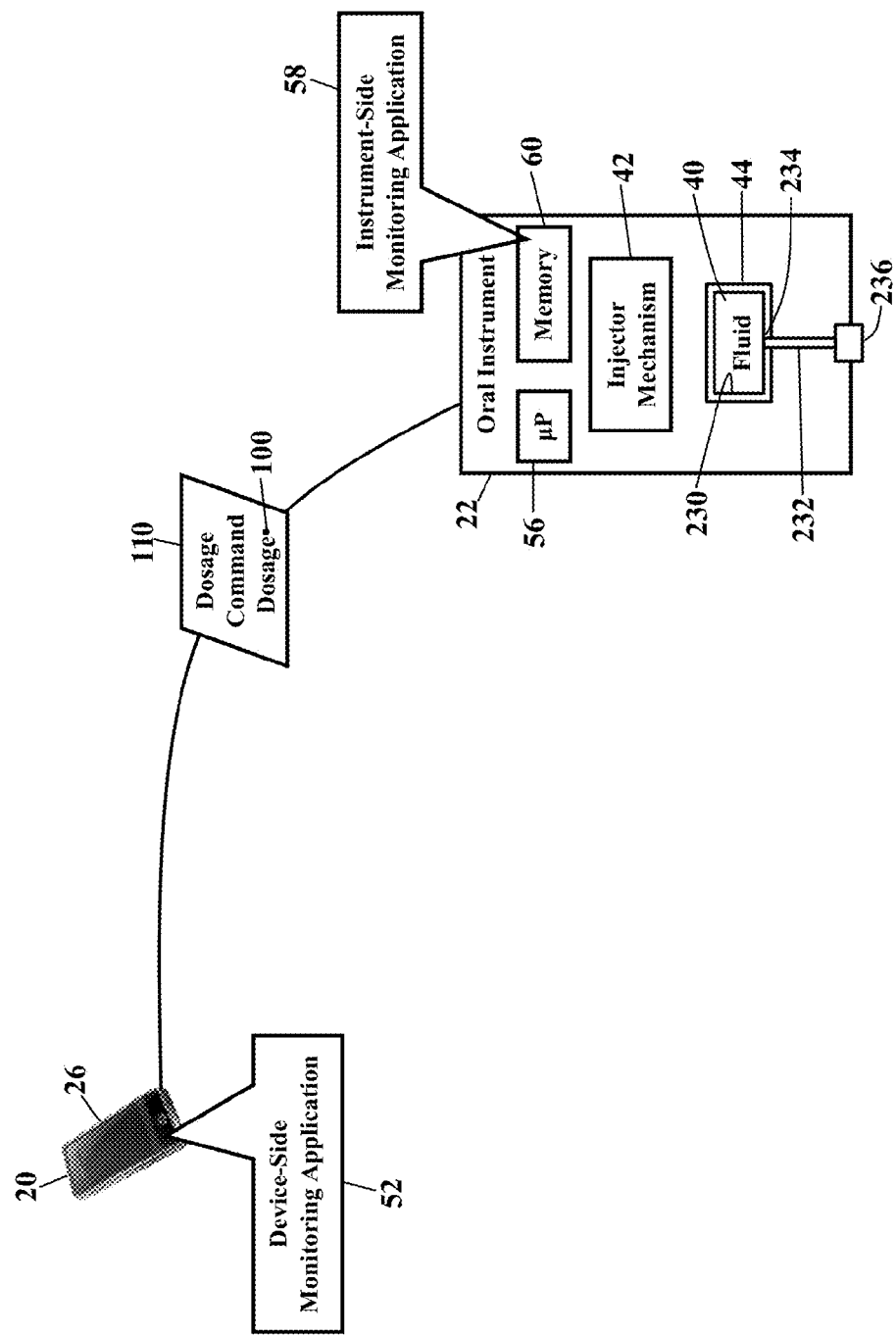
FIGS. 21-22 are detailed block diagrams of an injector mechanism, according to exemplary embodiments.
Figure 22:
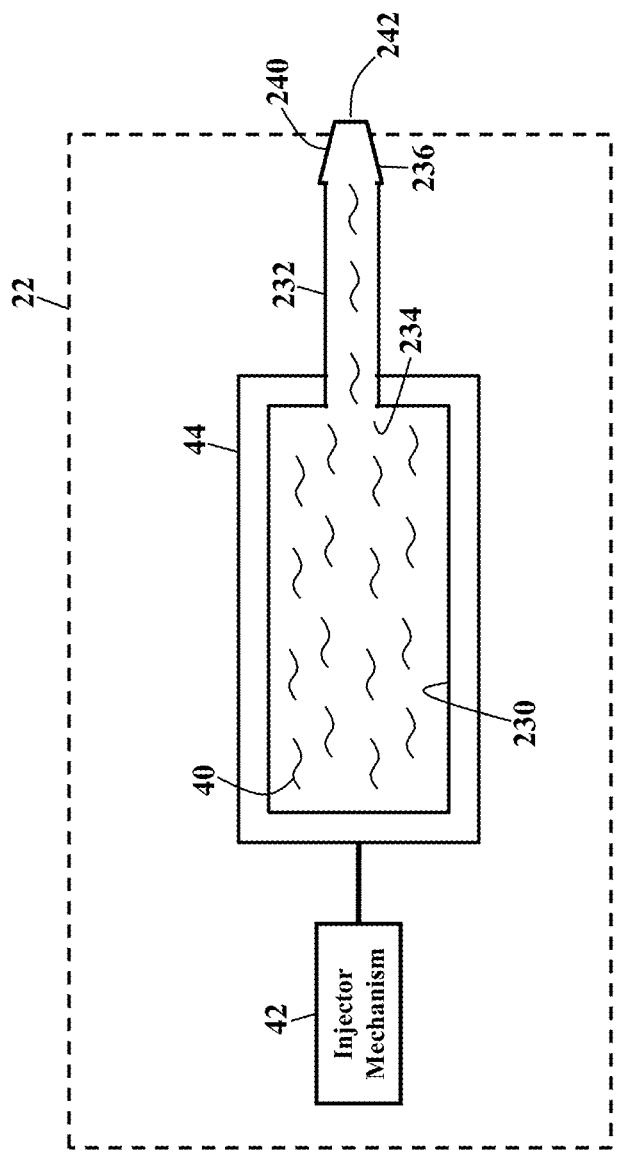

FIGS. 21-22 are more detailed block diagrams of the injector mechanism 42, according to exemplary embodiments. When the oral instrument 22 receives the dosage command 110, the instrument-side monitoring application 58 causes the processor 56 to activate the injector mechanism 42. The injector mechanism 42 may compress the fluid 40 in the reservoir 44. The fluid reservoir 44 has one or more sidewalls 230 that contain the fluid 40 within an interior of the oral instrument 22. A fluidic path 232 communicates the fluid 40 from an inlet 234 in the fluid reservoir 44 to an outlet 236. Because the injector mechanism 42 compresses the fluid 40, the fluid 40 flows under pressure through the fluidic path 232 and discharges from the outlet 236. While the outlet 236 may be located at any exterior location of the oral instrument 22, the outlet 236 is preferably located on an exterior surface in an oral portion of the oral instrument 22. Because the fluid 40 is preferably ingested, the outlet 236 is located in or on a portion of the oral instrument 22 that is inserted into the user's mouth. The outlet 26, for example, is configured to discharge the fluid 40 near a bristled head of the toothbrush or in proximity to the bowl of the spoon (the toothbrush and spoon are illustrated, respectively, as reference numerals 28 and 30 in FIG. 1).

FIG. 22 illustrates a nozzle 240. The nozzle 240 is illustrated in an enlarged view for clarity of features. The nozzle 240 may have a central orifice 242 that diffuses the fluid 40 as it discharges from the outlet 236 of the fluidic path 232. The diameter and/or shape of the central orifice 242 may thus be chosen to spray, stream, or mist the discharging fluid 40. The fluid 40 in the fluid reservoir 44, for example, may be an appetite suppressant that is sprayed on ingested food to reduce consumption. The fluid 40 may be a flavor enhancer that complements flavors in food. The fluid 40, for example, may be a concentrated gravy, liquid spice, or refreshment that is dispensed from the central orifice 242. The fluid 40, however, may also alter a taste of food to discourage consumption. The fluid 40, as earlier mentioned, may be a liquid medicine that is orally dispensed.

Figure 23:
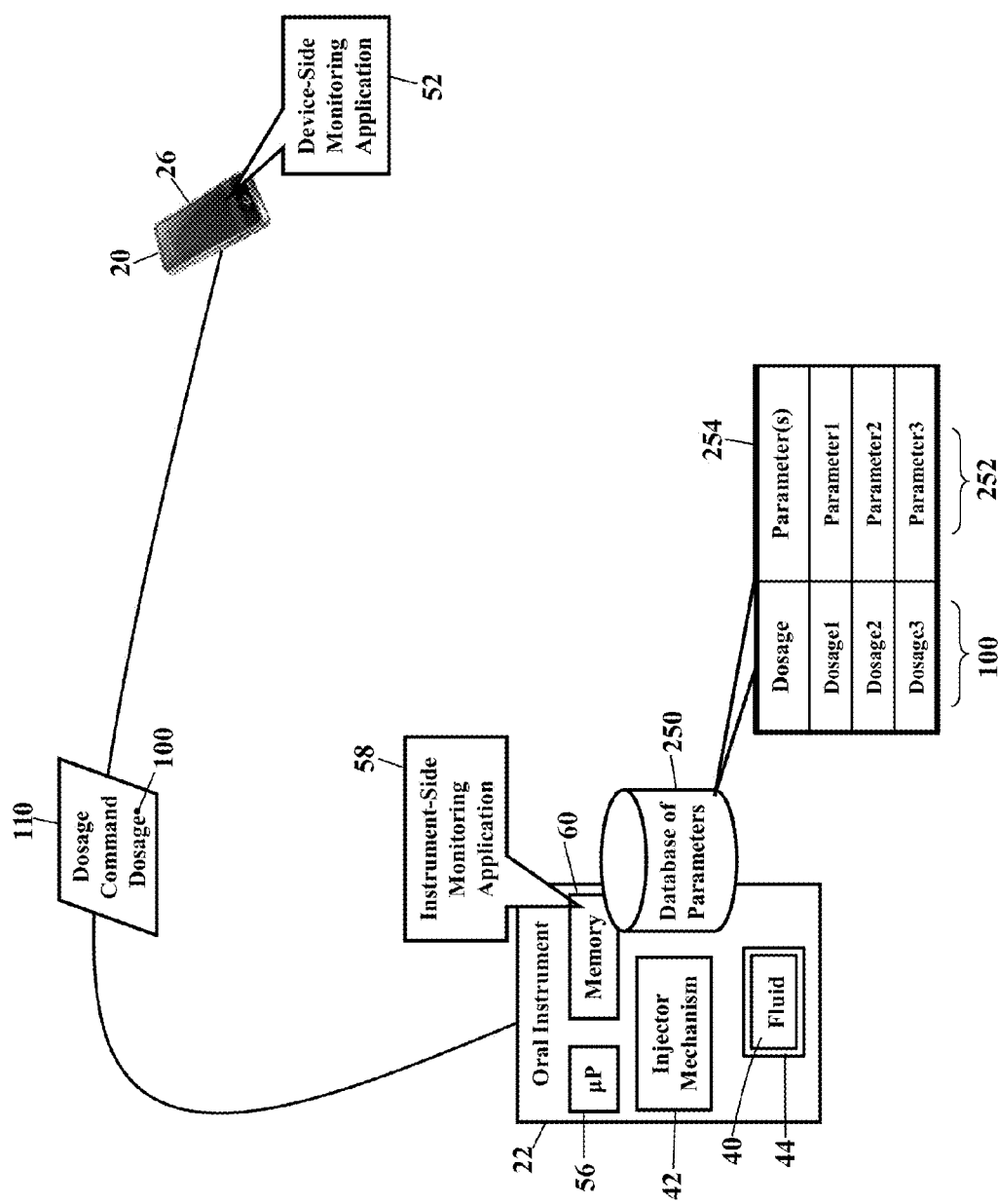
FIG. 23 is a block diagram illustrating operational parameters, according to exemplary embodiments.

FIG. 23 is a block diagram illustrating operational parameters, according to exemplary embodiments. Even though the dosage 100 is known (from the dosage command 110), the dosage 100 may need to be translated into parameters for the injector mechanism 42. A dosage 100 of "1 teaspoon," for example, is likely meaningless to the injector mechanism 42. The injector mechanism 42, instead, may require motor and/or pump parameters, such as voltages, currents, and/or displacements. That is, if the injector mechanism 42 is electromechanical, the injector mechanism 42 may only accept voltage and current parameters to inject the fluid 40. So, when the oral instrument 22 receives the dosage command 110, the instrument-side monitoring application 58 may consult a database 250 of parameters. The database 250 of parameters determines parameters 252 for actuating the injector mechanism 42, according to the required dosage 100. The database 250 of parameters is illustrated as a table 254 that maps, relates, or associates different dosages 100 to different parameters 252 for actuating the injector mechanism 42. The instrument-side monitoring application 58 queries the database 250 of parameters for the dosage 100 and retrieves the corresponding parameters 252 for actuating the injector mechanism 42. The parameters 252 may thus be a current and/or voltage at which the injector mechanism 42 is driven to dispense the required dosage 100. The parameters 252, however, may also include a linear displacement distance, pressure value, time of actuation, speed of displacement, or any other value required for operating the injector mechanism 42. Once the parameters 252 are known, the processor 56 is instructed to control the injector mechanism 42 using the parameters 252.

The communications device 20 may thus be agnostic to the oral instrument 22. That is, the communications device 20 need not care about the manufacturer or model of the oral instrument 22. All the communications device 20 need do is send the dosage command 110. The actual parameters 252 for accurately dispensing the dosage 100 are handled by the oral instrument 22. The oral instrument 22 may thus store its own operational parameters 252 that ensure the dosage 100 is correctly administered. The device-side monitoring application 52, in other words, need not store, retrieve, and interpret hundreds or thousands of parameters 252 associated with different manufacturers of toothbrushes, spoons, forks, and other oral utensils. The device-side monitoring application 52 need only send the required dosage 100, and the oral instrument 22 determines its own operational parameters 252. The device-side monitoring application 52 is thus relieved of the burden of supporting different oral instruments 22.

Figure 24:
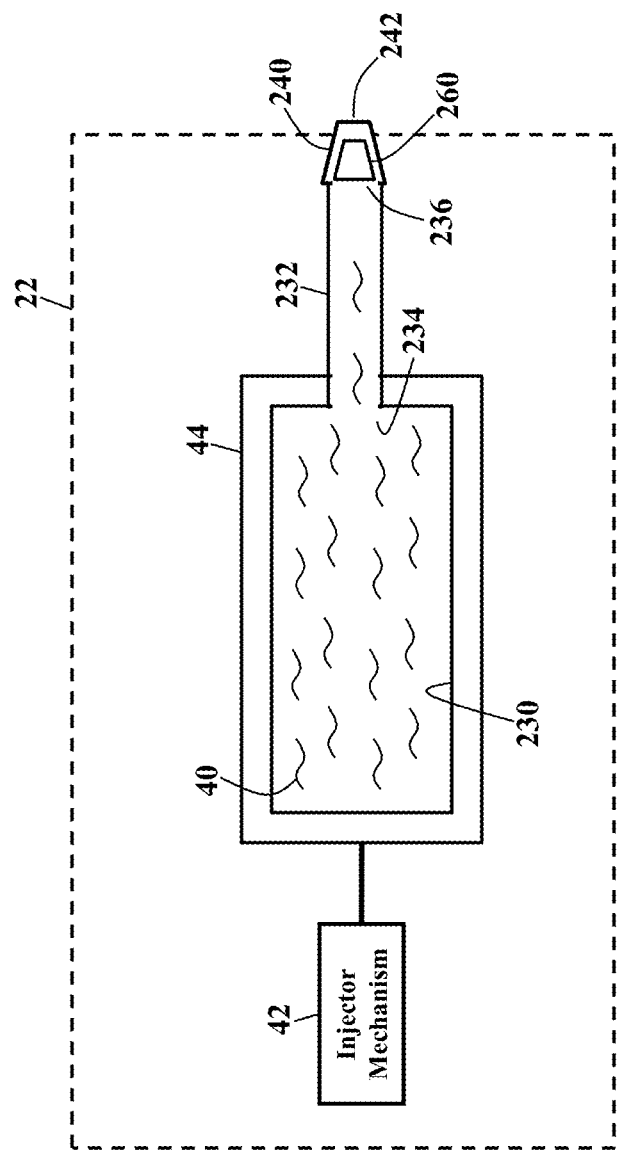
FIG. 24 is another detailed block diagram of the injector mechanism, according to exemplary embodiments.

FIG. 24 is another detailed block diagram of the injector mechanism 42, according to exemplary embodiments. FIG. 24 illustrates an enlarged view of a valve 260 in the oral instrument 22. Because the fluid 40 is pressurized, the fluid 40 may weep from the outlet 236 of the fluidic path 232. Exemplary embodiments may thus include the valve 260 to maintain pressure in the injector mechanism 42. The valve 260, for example, may be configured in proximity to the outlet 236 of the fluidic path 232. The valve 260 may open when pressure builds in the fluidic path 232, thus allowing the fluid 40 to discharge. The valve 260, however, may close when pressure falls. So, as the injector mechanism 42 operates to build up pressure for discharge, the valve 260 opens. When the injector mechanism 42 stops, pressure in the fluidic path 232 will drop, thus causing the valve 260 to close. While the valve 260 may be configured at any location along the fluidic path 232, a location in proximity to the outlet 236 may be preferred. A different location may require higher pressures to ensure the pressurized fluid 40 flows entirely along the fluidic path 232. Moreover, the valve 260 may be designed to prevent backflow, thus preventing saliva, toothpaste, and food from entering and clogging the fluidic path 232.

The injector mechanism 42 may be any electromechanical design. The injector mechanism 42, for example, may include a fluid press that compresses the fluid 40 in the fluid reservoir 44. A piston bears against the fluid 40 and moves or slides to compress the fluid 40. The piston connects to a rod that slides through an opening in the sidewall 230 of the fluid reservoir 44. The rod is electromechanically moved by the injector mechanism 42 according to the parameters 252 associated with the dosage 100. The piston may include a sealing ring to prevent or reduce pressure loss due to leakage of the fluid at the sidewall 230.

The injector mechanism 42 may include a pump. The pump is configured to build hydraulic pressure in the fluid reservoir 44. There are many different designs and configurations of pumps, so exemplary embodiments may be adapted for any pump. As the pump builds pressure in the fluid reservoir 44, the pressurized fluid 40 flows through the fluidic path 232 and discharges from the outlet 236.

Figure 25:
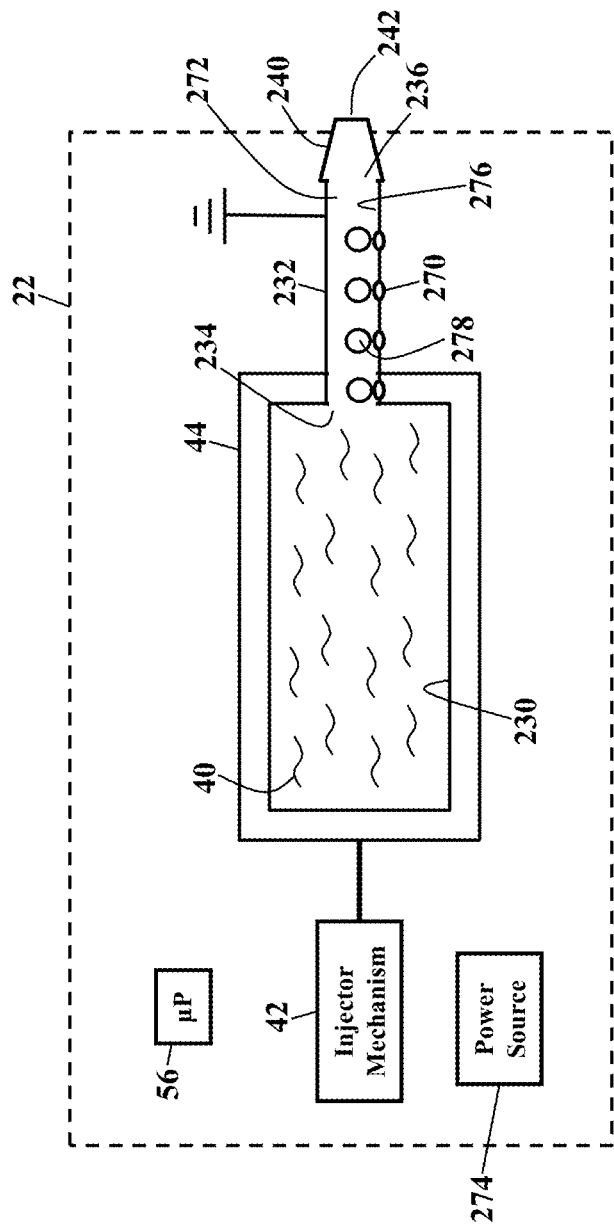
FIG. 25 is a schematic illustrating fluidic electrodes, according to exemplary embodiments.

FIG. 25 is a schematic illustrating an enlarged view of fluidic electrodes 270, according to exemplary embodiments. The electrodes are arranged in series along an interior 272 of the fluidic path 232. Each electrode 270 is electrically activated by a voltage from a power source 274. An interior wall 276 of the fluidic path 232 may be electrically grounded to electrical ground. The instrument-side monitoring application 58 commands the processor 56 to sequentially activate the electrodes 270. As the electrodes 270 are sequentially activated, the fluid 40 will transfer from the fluid reservoir 44 in discrete droplets 278. Each droplet 278 is electrostatically attracted to an adjacent, activated electrode 270. By sequentially activating the electrodes 270, the droplets 278 of the fluid 40 may be transferred along the fluidic path 232. The droplets 278 thus convey along the fluidic path 232 to the outlet 236 for dispensation.

Figure 26:
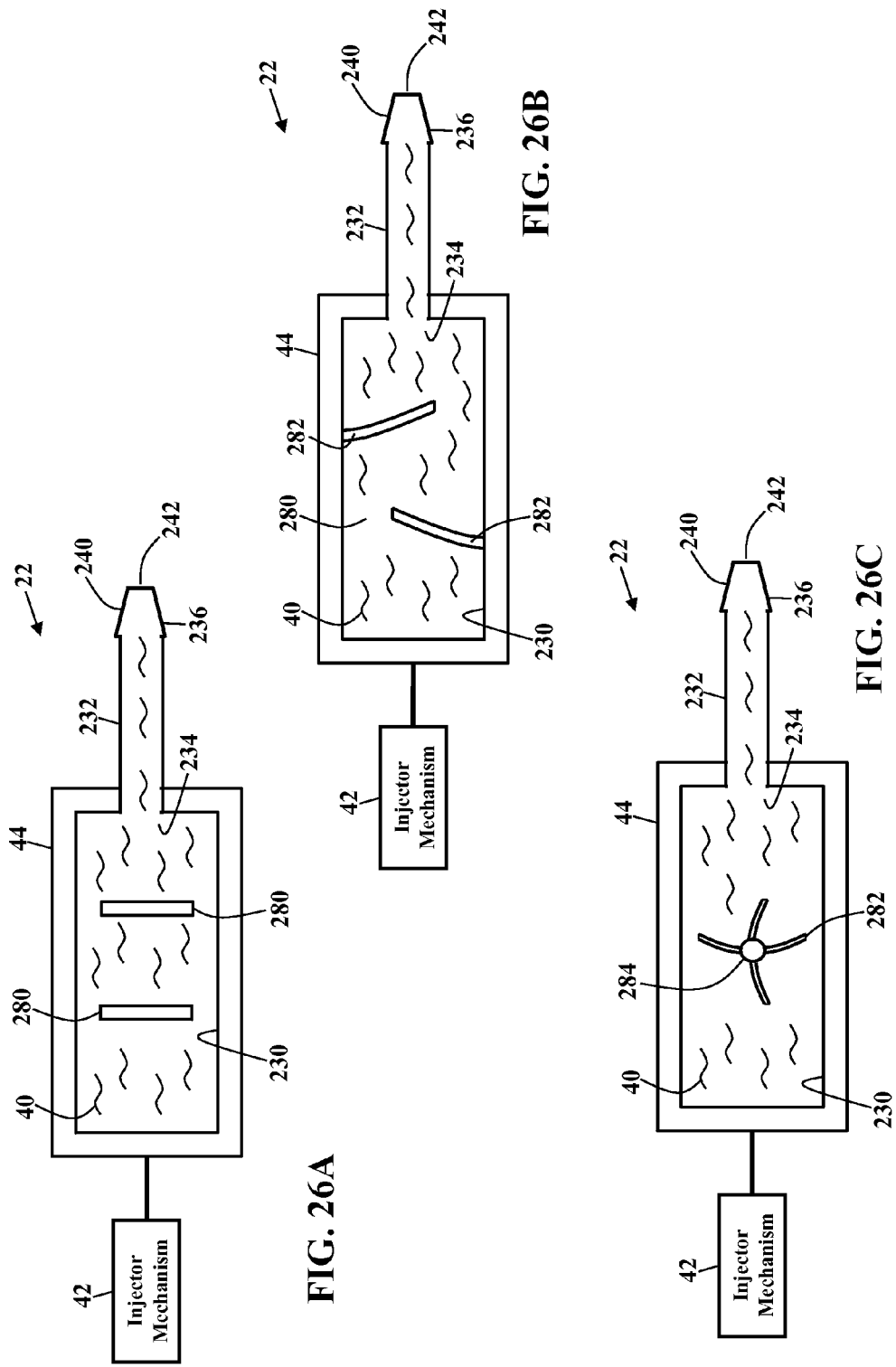
FIG. 26A-26C are schematics illustrating means for reducing turbulence in a fluid reservoir, according to exemplary embodiments.

FIG. 26 is a schematic illustrating means for reducing turbulence in the fluid reservoir 44, according to exemplary embodiments. The fluid reservoir 44 is again illustrated in an enlarged view for clarity of details. As the oral instrument 22 is manually used, the fluid 40 in the reservoir 44 may become turbulent. When the user brushes their teeth, for example, the relatively violent, back-and-forth motion of the toothbrush 28 may cause turbulence in the fluid 40 contained in the fluid reservoir 44. When the fluid 40 is subjected to turbulent conditions, air bubbles may form in the fluid reservoir 44. These air bubbles may reduce the pressure in the fluid reservoir 44, thus reducing dispensation of the fluid 40 from the oral instrument 22.

Exemplary embodiments may thus include means for reducing turbulence in the fluid reservoir 44. FIG. 26A, for example, illustrates one or more baffles 280 in the fluid reservoir 44. If the fluid 40 agitates during use, the baffle 280 dampens motion of the fluid 40 to reduce turbulence. The baffle 280 may be a partial partition or wall in the interior of the fluid reservoir 44. Each baffle 280 may have a rigid or pliable design, depending on the level of turbulence. FIG. 26B illustrates one or more dampening fingers 282 that reduce turbulence. Each finger 282 outwardly extends from the interior wall 230 of the fluid reservoir 40. Each finger 282 sways to dampen motion of the fluid 40 in the reservoir 44. FIG. 26C also illustrates the fingers 282, but here the fingers 282 outwardly extend from a central post 284. The central post 284 upwardly or outwardly projects from the interior wall 230 of the fluid reservoir 40. There may be any number of fingers 282 that extend from the central post 284, thus resembling a spider or crab configuration. If the oral instrument 22 experiences violent motions, the fingers 282 reduce turbulence in the fluid 40. Because the fingers 282 illustrated in FIG. 26C radially extend from the central post 284, the fingers 282 may dampen any directional flow of the fluid 40. That is, whether the oral instrument 22 is shook up or down, left or right, the radially extending fingers 282 dampen in any direction.

The baffle 280 and the finger 282 may be hydraulically tuned. Because the fluid reservoir 44 may be refilled with different liquids, the different liquids will have different viscosities. Some liquids, then, may become easily disturbed (such as mouthwash), while other liquids are thicker and less easily disturbed (such as cough syrup). Some designs of the baffle 280 and the finger 282 may thus be better suited to lower viscosities of fluids, while other designs may be better for higher viscosities. Exemplary embodiments, then, may include varying cross-sectional designs for the baffle 280 and the finger 282. That is, each baffle 280 and/or finger 282 may have a varying cross-section from an initial cross-section to a lesser, final cross-section. The lesser, initial cross-section, for example, may be configured at the interior wall 230 of the fluid reservoir 40. As the baffle 280 and/or the finger 282 outwardly extend, each may reduce in cross-section. A tip of the baffle 280 and/or the finger 282, having the lesser, final cross-section, may thus dampen the fluid 40 during small motions of the oral instrument 22. Larger motions will progressively deflect down toward the base at the interior wall 230. The baffle 280 and the finger 282 thus sway during turbulent conditions in the reservoir 44. Their swaying movement dampens the motion of the fluid 40 in the reservoir 44, thus reducing formation of air bubbles. While the baffle 280 and the finger 282 may be made from any material, the material is preferably unaffected by the chemical composition of the fluid 40. A mouthwash, for example, may have a high alcohol content, so the baffle 280 is preferably unaffected by alcohol.

Figure 27:
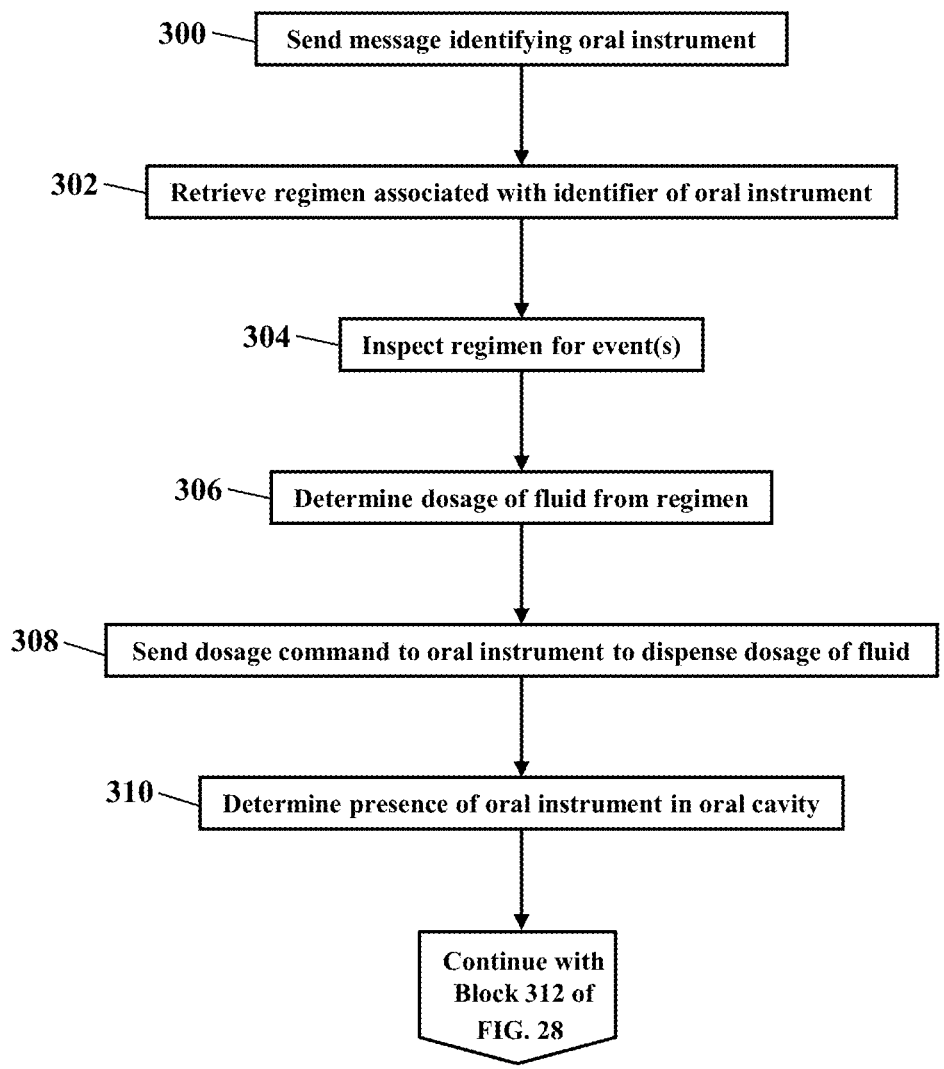
FIG. 27-28 are flowcharts illustrating a method or algorithm for monitoring health, according to exemplary embodiments.
Figure 28:
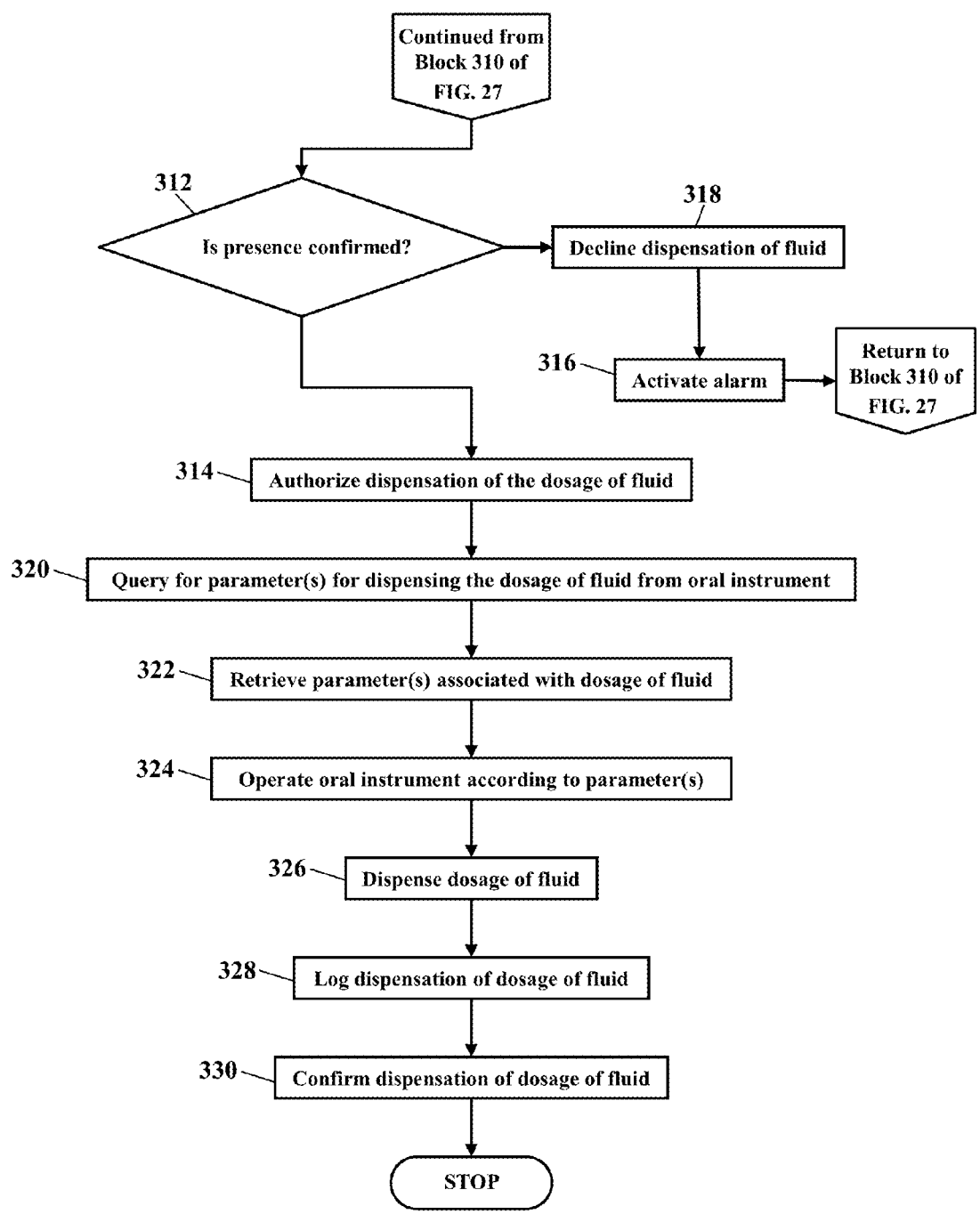

FIGS. 27-28 are flowcharts illustrating a method or algorithm for monitoring health, according to exemplary embodiments. The message 70 is sent identifying the oral instrument 22 (Block 300). The regimen 36 is retrieved that is associated with the identifier 72 of the oral instrument 22 (Block 302). The regimen 36 is inspected for events (Block 304). The dosage 100 of the fluid 40 is determined from the regimen 36 (Block 306). The dosage command 110 is sent to instruct the oral instrument 22 to dispense the dosage 100 of the fluid 40 (Block 308). Presence of the oral instrument 22 in an oral cavity is determined (Block 310).

The algorithm continues with FIG. 28. If the presence is confirmed (Block 312), then dispensation of the dosage 100 is authorized (Block 314). If the presence is unconfirmed (Block 312), the dispensation is denied (Block 316). The alarm 210 is activated (Block 318) to alert of the dosage requirement. Because the fluid 40 may be a required medicine, the algorithm may continually monitor for the presence of the oral instrument 22 in the oral cavity (e.g., return to Block 310 of FIG. 27).

When dispensation is authorized (Block 314), a query is made for parameters for dispensing the dosage 100 of the fluid 40 from the oral instrument 22 (Block 320). The parameter 252 is retrieved that is associated with the dosage 100 of the fluid 40 (Block 322). The oral instrument 22 is operated according to the parameter 252 (Block 324). The dosage 100 of the fluid 40 is dispensed (Block 326). The dispensation is logged in the electronic journal 204 (Block 328). The confirmation message 70 may be sent to confirm dispensation (Block 330).

Figure 29:
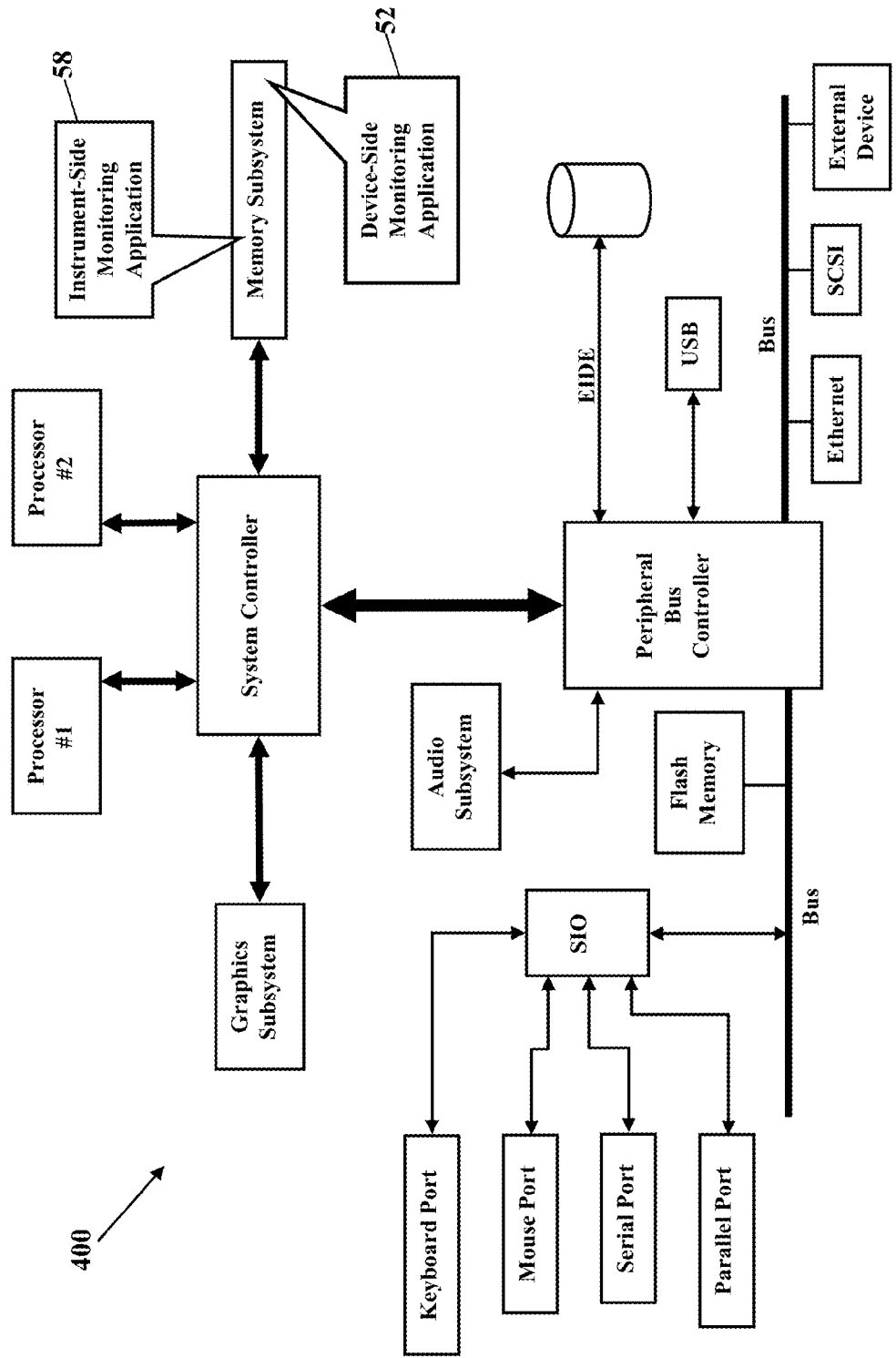
FIGS. 29-30 depict still more operating environments for additional aspects of the exemplary embodiments.

FIG. 29 is a schematic illustrating still more exemplary embodiments. FIG. 29 is a generic block diagram illustrating the device-side monitoring application 52, and/or the instrument-side monitoring application 58, operating within a processor-controlled device 400. As the previous paragraphs explained, the device-side monitoring application 52 and the instrument-side monitoring application 58 may operate in any processor-controlled device 400. FIG. 29, then, illustrates the device-side monitoring application 52 and the instrument-side monitoring application 58 stored in a memory subsystem of the processor-controlled device 400. One or more processors communicate with the memory subsystem and execute the device-side monitoring application 52 and the instrument-side monitoring application 58. Because the processor-controlled device 400 illustrated in FIG. 29 is well-known to those of ordinary skill in the art, no detailed explanation is needed.

Figure 30:
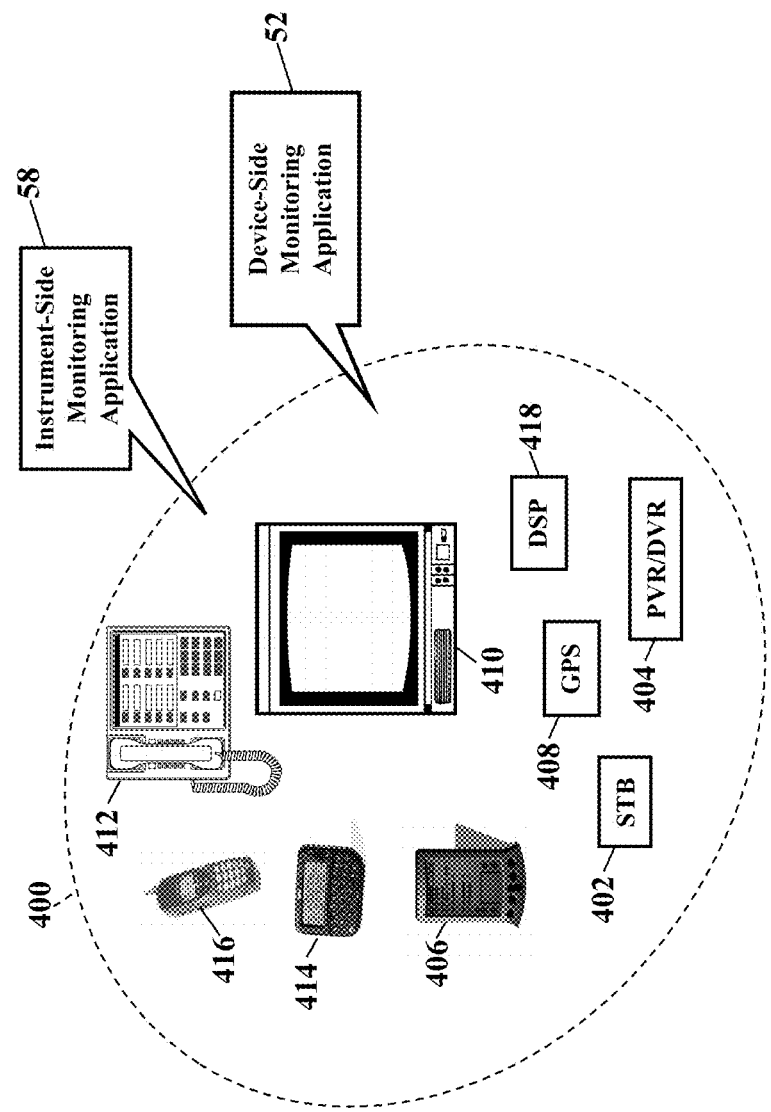

FIG. 30 depicts still more operating environments for additional aspects of the exemplary embodiments. FIG. 30 illustrates that the exemplary embodiments may alternatively or additionally operate within other processor-controlled devices 400. FIG. 30, for example, illustrates that the device-side monitoring application 52, and/or the instrument-side monitoring application 58, may entirely or partially operate within a set-top box ("STB") (402), a personal/digital video recorder (PVR/DVR) 404, personal digital assistant (PDA) 406, a Global Positioning System (GPS) device 408, an interactive television 410, an Internet Protocol (IP) phone 412, a pager 414, a cellular/satellite phone 416, or any computer system, communications device, or any processor-controlled device utilizing a digital signal processor (DP/DSP) 418. The device 400 may also include watches, radios, vehicle electronics, clocks, printers, gateways, mobile/implantable medical devices, and other apparatuses and systems. Because the architecture and operating principles of the various devices 400 are well known, the hardware and software componentry of the various devices 400 are not further shown and described.

Exemplary embodiments may be physically embodied on or in a computer-readable storage medium. This computer-readable medium may include CD-ROM, DVD, tape, cassette, floppy disk, memory card, and large-capacity disks. This computer-readable medium, or media, could be distributed to end-subscribers, licensees, and assignees. A computer program product comprises processor-executable instructions for monitoring health, as the above paragraphs explained.

While the exemplary embodiments have been described with respect to various features, aspects, and embodiments, those skilled and unskilled in the art will recognize the exemplary embodiments are not so limited. Other variations, modifications, and alternative embodiments may be made without departing from the spirit and scope of the exemplary embodiments.

What is claimed is:

1. A system, comprising:
    a processor; and
    a memory storing code that when executed causes the processor to perform operations, the operations comprising:
    sending, via a communications network, a message addressed to a network address, the message identifying an oral instrument;
    receiving a dosage command associated with the network address, the dosage command specifying a dosage of fluid to be dispensed from the oral instrument;
    determining a presence of the oral instrument in an oral cavity; and
    authorizing dispensation of the dosage of fluid from the oral instrument in response to the presence.

2. The system of claim 1, wherein the operations further comprise:
    detecting saliva in the oral cavity; and
    determining the presence in response to detection of the saliva.

3. The system of claim 2, wherein the operations further comprise denying the dispensation of the dosage of fluid if the saliva is undetected.

4. The system of claim 1, wherein the operations further comprise:
    receiving a temperature associated with the oral instrument;
    comparing the temperature to a threshold; and
    determining the presence in response to the temperature satisfying the threshold.

5. The system of claim 4, wherein the operations further comprise denying the dispensation of the dosage of fluid if the temperature fails to satisfy the threshold.

6. The system of claim 1, wherein the operations further comprise:
    receiving a motion associated with the oral instrument;
    comparing the motion to a threshold indicating acceptable movement associated with the oral instrument; and
    determining the presence in response to the motion satisfying the threshold.

7. The system of claim 6, wherein the operations further comprise activating an alarm when the dispensation is due.

8. The system of claim 6, wherein the operations further comprise denying the dispensation of the dosage of fluid if the motion fails the threshold.

9. The system of claim 1, wherein the operations further comprise maintaining a journal of dispensations from the oral instrument.

10. The system of claim 1, wherein the operations further comprise sending a notification of the dispensation to the network address.

11. The system of claim 10, wherein the operations further comprise logging the notification in a journal.

12. The system of claim 1, wherein the operations further comprise denying the dispensation of the dosage of fluid if the presence is undetermined.

13. The system of claim 1, wherein the operations further comprise activating an injector in response to the dosage command.

* * * * *